United States Patent
Uggeri et al.

Patent Number: 5,660,814
Date of Patent: Aug. 26, 1997

[54] IODINATED PARAMAGNETIC CHELATES, AND THEIR USE AS CONTRAST AGENTS

[75] Inventors: Fulvio Uggeri; Pier Lucio Anelli; Franco Fedeli; Marcella Murru; Christoph De Haen, all of Milan, Italy

[73] Assignee: Dibra S.p.A., Milan, Italy

[21] Appl. No.: 448,476

[22] PCT Filed: May 25, 1994

[86] PCT No.: PCT/EP94/01677

§ 371 Date: May 30, 1995

§ 102(e) Date: May 30, 1995

[87] PCT Pub. No.: WO94/27644

PCT Pub. Date: Dec. 8, 1994

[30] Foreign Application Priority Data

Jun. 2, 1993 [IT] Italy .................... MI93A1155
Jun. 15, 1993 [IT] Italy .................... MI93A1274

[51] Int. Cl.⁶ .................... A61K 49/00; G01N 31/00; G01N 33/48
[52] U.S. Cl. .................... 424/9.36; 424/9.4; 424/9.42; 424/9.1; 534/16
[58] Field of Search .................... 424/1.11, 9.1, 424/9.3, 9.36, 9.4, 9.42; 534/10–16

[56] References Cited

U.S. PATENT DOCUMENTS

| | | | |
|---|---|---|---|
| 5,182,370 | 1/1993 | Folder et al. | 534/16 |
| 5,242,683 | 9/1993 | Klaveness | 424/9.1 |
| 5,324,503 | 6/1994 | Lin et al. | 424/9.1 |
| 5,403,576 | 4/1995 | Lin et al. | 424/9.1 |
| 5,525,328 | 6/1996 | Bacon et al. | 424/9.45 |

FOREIGN PATENT DOCUMENTS 9101149 2/1991 WIPO.
9316375 8/1993 WIPO.

OTHER PUBLICATIONS

Weichert et al (1986). J. Med. Chem., vol. 29, pp. 2457–2465, "Potential Tumor or Organ Imaging Agents. 27. Polyiodinated 1,3-disubstituted and 1,2,3-trisubstituted Triacylglycerols".

Kwan et al (1988). American Journal of Neuroradiology, vol. 9, No. 3, pp. 523–531, "MR Evaluation of Neurovascular Lesions After Endovascular Occulsion with Detachable Balloons".

Rofu Fortschr. Gelo. Rontgenstr. Neuen Bildgebnden Verfahren, (1994) vol. 160, No. 4, pp. 349–352, "Signalverhalten Von Verschiedenen Röntgen–Kontrastmitteln Sowie Deren Wechselwirkung Mit Gadolinium–DTPA in der MRT" (English Abstract).

Primary Examiner—John Kight
Assistant Examiner—Dameron L. Jones
Attorney, Agent, or Firm—Bucknam and Archer

[57] ABSTRACT

Novel compounds containing a polyiodinated aromatic or heteroaromatic residue and their chelate complexes with ions of metal elements with atomic number from 20 to 31, 39, from 42 to 44, 49 and from 57 to 83, and their salts with physiologically tolerable organic and inorganic bases are useful contrast agents for preparation of diagnostic formulations to obtain images of organs and/or tissues of human and animal body through the use of nuclear magnetic resonance or X-rays or the combination of both nuclear magnetic resonance and X-rays.

15 Claims, No Drawings

IODINATED PARAMAGNETIC CHELATES, AND THEIR USE AS CONTRAST AGENTS

The chemistry of coordination compounds concerns metal complexes with suitable chelating agents, but many of its concepts can be extended to chemistry and biochemistry.

The use in medicine of a high number of chelating agents is well documented, for instance, as stabilizing agents for pharmaceutical preparations, as antidotes in case of ingestion of toxic metal species and as carriers for the administration of metal species (i.e. ions or atoms) through diagnostic techniques such as X-rays, nuclear magnetic resonance and scintigraphy.

Especially for NMR imaging, pharmaceutical paramagnetic compositions are now well known and more extensively investigated. They preferably contain complex chelating agents of bi- or trivalent metal ions with aminopolycarboxylic acid and/or their derivatives or analogues.

These compounds showed a good capacity of influencing proton relaxation times in NMR imaging, producing images of organs or tissues which, otherwise, couldn't be distinguished from the near regions, Many of these contrast agents have already been suggested in literature and the following patent list can be cited as an example, even though indicative and partial: EP-A-71564 (Schering), EP-A-130934 (Schering), U.S. Pat. No. 4,615,879 (Runge), DE-A-3401052 (Schering), EP-A-230893 (Bracco), EP-A-185899 (Nycomed), EP-A-186947 (Nycomed) EP-A-165728 (Nycomed), U.S. Pat. No. 4,647,447 (Schering), U.S. Pat. No. 4826673 (Mallinckrodt), U.S. Pat. No. 4,639,365 (Sherry), EP-A-299795 (Nycomed), EP-A-258616 (Salutar), WO 8905802 (Bracco).

It has been now surprisingly found, and it is one of the objects of this invention, a method to improve the capacity of paramagnetic metal chelates of influencing proton relaxation time s during NMR imaging and thanks to it, a totally new class of compounds has been prepared, representing another characteristic object of this invention.

This method relies on the insertion in the same molecular structure of a paramagnetic substance and a X-ray opaque polyiodinated component.

The paramagnetic component comprises a paramagnetic metal ion and, as chelating part, the residue of a cyclic or acyclic aminopolycarboxylic acid, or of an aminopolyphosphonic, aminopolyphosphinic, aminopolysulfonic, aminopolysulfinic acid and/or derivatives or analogues. To this structure, a radiopaque residue, comprising at least an aromatic or heteroaromatic polyiodinated moiety, with radiopaque properties, can be bound, via known synthetic steps.

As a non-limiting example, the structure of the chelating component can be formed by the residue of one of the following chelating agents: EDTA (ethylenediaminotetraacetic acid), DTPA (U.S. Pat. No. 4,647,447: Schering), DTPA-bismethylamide (WO 8602841: Salutar); DOTA (DE-A-3401052: Schering), DO3A and MP-DO3A (EP-A-292689: Squibb), BOPTA (EP 230893: Bracco), DPDP (EP-A-290047: Salutar), DOTMA (Int. Jour. Rad/Appl and Instr, Pt. B, 15(1) 1988, 9–15), MCTA (EP-A-287465: Guerbet), EOB-DTPA (EP-A-40-5704: Schering), BT-DO3A (EP-A-448191: Schering), DTPA hydroxyalkyl amides (U.S. Pat. No. 4,826,673: Mallinckrodt and EP-A-130934: Schering), as well as the macrocyclic chelating agents disclosed in EP-A-440606 (Bracco).

The iodinated component can be constituted by the residue of a known X-ray contrast agent, ionic and/or non-ionic, monomeric or dimeric, including a polyiodinated aromatic nucleus or two polyiodinated aromatic nuclei.

This residue can, for instance, preferentially belong to one of the following compounds (USAN and USP Dictionary of Drug Names, Ed. 1993): acetrizoic acid, diprotizoic acid, iobenzamic acid, iobutoic acid, iocarmic acid, iocetamic acid, iopanoic acid, iopronic acid, iothalamic acid, diatrizoic acid, iodoxamic acid, ioglycic acid, ioglycamic acid, iolidonic acid, iolixanic acid, iomorinic acid, ioprocemic acid, iosephamic acid, ioseric acid, iotetric acid, iotrizoic acid, iotroxic acid, ioxaglic acid, metrizoic acid, iodamide, iodipamide, iopamidol, iomeprol, iohexol, ioversol, metrizamide, iotrolan, iodecimol, iodixanol, ioglucol, ioglucomide, ioglunide, iogulamide, iopentol, iopidol, iopyrol (EP-A-431838, Squibb), iopromide, iosarcol, iosimide, iotasul, iotriside, ioxilan, iofratol (WO 9208691, Bracco).

Recently [19.08.1993] the application WO 9316375 (Mallinckrodt) was published regarding a similar general class of compounds. Particularly, it claims compounds comprising a chelating moiety with at least one heavy metal ion chelated, a linker portion and an iodinated moiety. The chelating agent can be a polyaminopolycarboxylic acid either linear, such as EDTA, DTPA, or cyclic, such as DTPA, DO3A, HP-DO3A or derivatives thereof; also disclosed are desferrioxamine derivatives, cryptands, calixarenes and chelating polymers.

The aim of Mallinckrodt Application seems to provide improved contrast agents for intravascular and central nervous system visualisation which can be used as either X-ray or MRI contrast agents. No data, however, are given supporting these statements.

Also very poor is the experimental section describing the preparation of only 2 compounds.

This invention refers to new compounds of general formula (Ia) and (Ib):

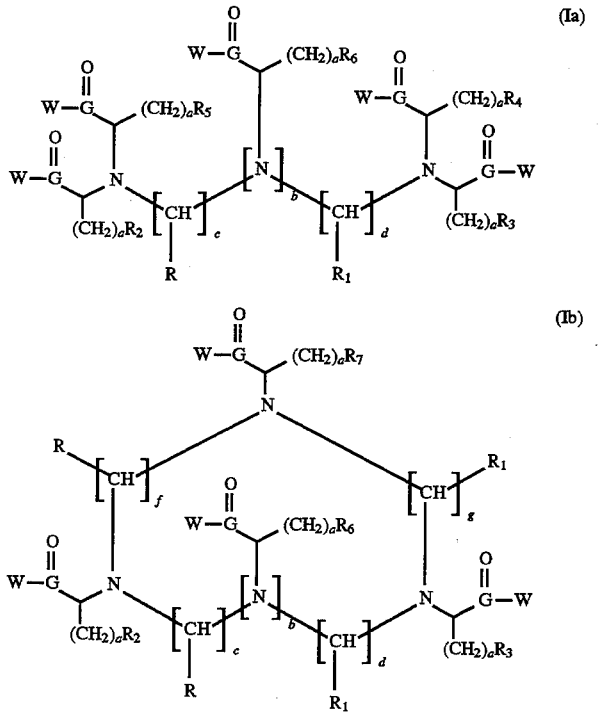

wherein:
a, b, which are the same or different, are 0 or 1,
c, d, which are the same or different, can be an integer from 1 to 4, f, g, which are the same or different; are an integer from 2 to 4, R, $R_1$, which are the same or different, are H, or a $C_1$-$C_8$ straight, branched or alicyclic alkyl group, or a $C_1$-$C_6$ straight or branched hydroxyalkyl group, containing 1–5 OH groups, or an alkoxyalkyl or hydroxyalkoxyalkyl group, or they are one aryl, alkylaryl, aryloxy, benzyloxy or heteroaryl residue, where the aromatic nucleus is substituted or not by one or more halogen, alkyl, hydroxyalkyl, hydroxyl alkoxyl, trifluoromethyl, carboxyl, amino, carbamoyl, anilido, cyano, thiocyano, nitro, mercapto, thioalkyl, sulforyl, ,sulfonyl, phosphoryl, phosphonyl group, or R and $R_1$, taken together, are a trimethylene or tetramethylene residue, $R_2$–$R_7$, which are the same or different, are H, or a $C_1$-$C_8$ straight, branched or alicyclic alkyl group, or a $C_1$-$C_8$ alkoxyalkyl group, or a group of formula —$CH_2$—O-Y—, where the residue Y is H, a $C_{1-C8}$ straight, branched or alicyclic alkyl group, or an aryl, alkylaryl or heteroaryl nucleus, in which the aromatic nucleus is substituted or not by one or more halogen, alkyl, hydroxyalkyl, hydroxyl, alkoxyl, trifluoromethyl, carboxyl, amino, carbamoyl, anilido, cyano, thiocyano, nitro, mercapto, thioalkyl, sulforyl, sulfonyl, phosphoryl, phosphonyl group, or the substituents from $R_2$ to $R_7$ can be the residue Z of formula:

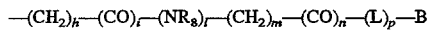

wherein:

h, i, l, n, p are integers from 0 to 1, m is an integer from 0 to 20,

B is an X-ray opaque, ionic or non-ionic, aromatic or heteroaromatic residue, containing at least a functionalized iodinated aromatic nucleus, being said B group bound to the remaining part of Z through one of the non-iodinated positions of the aromatic nucleus, L is —$NR_8$— or —O— and $R_8$ is H, or the residue of formula —$(CH_2)_m$—$(CO)_n$—$(NH)_p$—B, wherein m, n, p and B are as above defined, G is a carbon, sulfur, phosphorus atom, or —SO—, —$SO_2$—, —PO—, —$PO_2$—, W is H, or one of the groups: Z, —O—$R_9$ or —N($R_{10}$)—$(CH_2)_q$—$R_{11}$, wherein:

Z is as above defined, $R_9$ is H or a $C_1$-$C_8$ straight, branched or alicyclic alkyl group, or a $C_1$-$C_6$ straight, branched hydroxyalkyl group, containing 1–5 OH groups, or an alkoxyalkyl or hydroxyalkoxyalkyl group, or $R_9$ is a polyoxaalkyl residue containing from 1 to 15 oxygen atoms and from 3 to 45 carbon atoms, q is an integer from 0 to 6, $R_{10}$ equal or different from $R_{11}$, is H or a $C_1$-$C_8$ straight, branched or alicyclic alkyl group, or a $C_1$-$C_6$ straight, branched hydroxyalkyl group, containing 1–5 OH groups, or an alkoxyalkyl or alkoxyhydroxyalkyl group, or a residue Z as above defined, $R_{11}$ is defined as $R_{10}$ and in addition, when q is different from 0, it can also be one of the two groups —CO—$NR_{12}R_{13}$ or —$NR_{12}R_{13}$ wherein $R_{12}$ and $R_{13}$ are defined as $R_{10}$ and $R_{11}$, and when q is equal to 0, then $R_{10}$ and $R_{11}$ can be bound together to represent a $C_2$-$C_6$ alkylene group which can be interrupted by —O—, —S—, —N— atoms, with the proviso that, at least one of the substituents from $R_2$ to $R_7$ must be a residue Z, or at least one of the groups W must be or include a residue Z.

This invention also includes chelate complexes of said compounds of formula (Ia) and (Ib) with ions of metal elements with atomic number from 20 to 31, 39, from 42 to 44, 49 and from 57 to 83, and the salts thereof with physiologically tolerable organic bases, selected from primary, secondary or tertiary amines or basic amino acids, or with inorganic bases whose cations are sodium, potassium, magnesium, calcium or mixtures of the same.

Particularly preferred are the compounds of general formula (IIa), (IIb), (IIc):

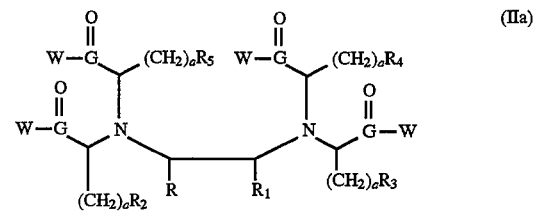

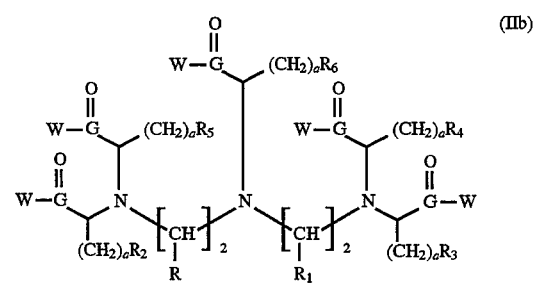

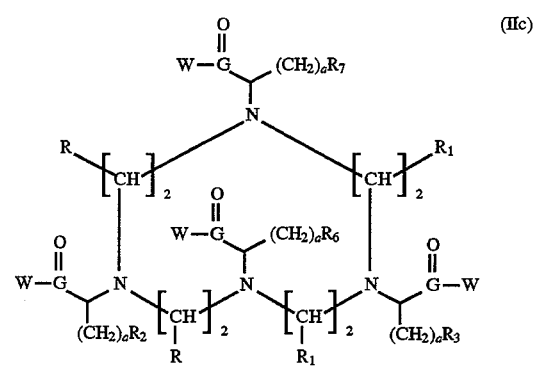

wherein a, R, $R_1$, $R_2$, $R_3$, $R_4$, $R_5$, $R_7$, G, W are as above defined, with the proviso that at least one of the $R_2$–$R_7$ substituents must be a residue Z as above defined, or at least one of the W group is or include said residue Z.

Equally preferred are the chelate complexes of said compounds of formula (IIa), (IIb), (IIc) with ions of metal elements with atomic number included from 20 to 31, 39, from 42 to 44, 49 and from 57 to 83 and their salts with physiologically tolerable organic bases, selected from primary, secondary or tertiary amines or basic amino acids, or with inorganic bases whose cations are sodium, potassium, magnesium, calcium or mixtures of the same.

Such derivatives, if necessary, can be chemically conjugated to suitable macromolecules or biomolecules, or fragments of the same, or encapsulated in suitable carriers such as liposomes.

This invention also includes the preparation of the products of general formula (Ia) and (Ib) and their salts, their uses and the deriving pharmaceutical compositions for diagnostic use.

The chelating agents of this invention and their salts have multiple applications. Non-limiting examples show their use in the recovery, separation, selective extraction of metal ions even at low concentration, or in therapy as detoxifying agents in case of intoxication from metals or radioisotopes, or as carriers of ions and in other cases well known by the experts of the fields.

In particular, the complex salts of general formula (Ia) and (Ib) with metal ions of the elements with atomic number included from 20 to 31, 39, from 42 to 44, 49 and from 57 to 83 which can be salified with physiologically tolerable organic or inorganic bases, or amino acids, are suitable for medical diagnosis as contrast media in nuclear medicine, MRI and X-ray diagnosis.

These derivatives, in view of their ideal diagnostic use, can be bound, or encapsulated into biomolecules, macromolecules or liposomes able to concentrate in the organ or in the tissue under examination.

As far as their diagnostic use is concerned, the chelate complexes of this invention, are surprisingly effective as MRI and X-ray contrast agents. Among them, $Gd^{(3+)}$ complexes are quite remarkable for their excellent stability, relaxivity, selectivity, X-ray opacifying properties and a particular organ tropism.

The new compounds of this invention meet the ideal characteristics of a contrast medium. They show a good tolerability, allowing a non-invasive action in diagnostic procedures, a good water-solubility and a reduced osmolality which make them particularly suited for their diagnostic use. And in vivo, they result to be organ specific. In fact, some of them, show preferential hepatobiliary elimination versus the renal route. Moreover, they are highly stable both in vivo and in vitro.

As a non-limiting example of their characteristics, in Example 9, in-vitro relaxivity values of some preferred compounds of this invention are compared to the available data for marketed paramagnetic compounds, that's to say Dotarem® (Gd-DOTA meglumine salt, marketed by Guerbet) and Magnevist® (Gd-DTPA meglumine salt, marketed by Schering) which are not only the nearest prior art, but at the same time the obvious reference for researchers who want to compare their products to the known technique.

As clearly remarked, the addition of at least one polyiodinated aromatic nucleus to the frame of a chelating agent deriving from an aminopolycarboxylic acid or a derivative thereof, has remarkably and surprisingly improved the paramagnetic properties of metal complexes of said new class of compounds.

The chelate complexes of this invention are very interesting multiaction contrast agents. In fact, they can be used in X-ray and MRI examinations. If needed, the two diagnostic procedures can be successively performed after a single administration.

As a non-limiting example, in Example 10, are reported the results of the radioscopic examination (50 kV, 0.8 mA), after the administration (1 rat/dose) of some preferred compounds of this invention.

The compounds of this invention can be used in various applications, since an intravasal, (such as intravenous, intraarterial, intracoronaric, intraventricular and so on), intrathecal, intraperitoneal, intralymphatic, intracavital and intraparenquimal administration can be performed. Both soluble and less soluble compounds are suited for oral or enteral administration, and therefore, in particular for the gastrointestinal tract imaging. For parenteral administration, they are preferably formulated as sterile aqueous solutions or suspensions, whose pH can range between 6.0 and 8.5. These sterile aqueous solutions or suspensions can be administered in concentrations of 0.002–1.0 Mol.

These formulations can be also lyophilised and supplied as such. For the gastrointestinal use or for body cavities injections they can be formulated as solutions or suspensions containing additives suitable, for instance, for viscosity control.

For oral administration, they can be formulated according to preparation methods commonly used in pharmaceutical technique, and in some cases as coated formulations in order to obtain an additional protection against the stomach acid pH values, which can cause the releasing of the particularly toxic metal ions. Other excipients, such as sweeteners and/or flavouring agents, can be added according to known techniques of pharmaceutical formulations.

Complex salts solutions or suspensions of this invention can be formulated as aerosol for aerosol-bronchography or instillation.

In the diagnostic field, the chelates of this invention can also be used as contrast media in nuclear medicine. In this case, the chelated metal ion is a radioisotope emitting particle such as $^{51}Cr$, $^{68}Ga$, $^{111}In$, $^{99}mTc$, $^{140}La$, $^{168}Yb$.

Metal ions able to form complex salts with the chelating agents of general formula (I) are especially bi- or trivalent ions of the elements with atomic number between 20–31, 39, 42, 43, 44, 49 or between 57 and 83; particularly preferred are $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$.

Preferred anions of inorganic acids possibly suited for the salification of chelate complexes of this invention include,. in particular, halide ions such as chlorides, bromides, iodides or other ions such as sulfate.

Preferred anions of organic acids suited for the above mentioned aim include those of acids commonly used in the pharmaceutical technique for the salification of basic substances, such as acetate, succinate, citrate, fumarate, maleate.

Preferred cations of inorganic bases suited for the salification of chelate complexes of this invention include in particular, alkaline or earth alkaline metal ions such as potassium, sodium, calcium, magnesium, or their mixtures.

Preferred cations of organic bases suited for the above mentioned aim include, among others, those of primary, secondary and tertiary amines such as ethanolamine, diethanolamine, morpholine, glucamine, N,N-dimethylglucamine and especially N-methylglucamine.

Preferred cations and anions of amino acids include, for example, those of lysine, arginine or ornithine.

Among macromolecules which can be conjugated to chelate complexes of this invention it is worthwhile to mention as non-limiting example the following ones: biomolecules, such as hormones (insulin), prostaglandins, steroid hormones, aminosugars, peptides, proteins (albumins, human seroalbumin), lipids, antibodies such as monoclonal antibodies, polysaccharidic chains.

Chelate complexes of this invention can also be encapsulated in liposomes used as uni- or multilamellar vesicles.

Among the compounds of this invention, the chelating agents of general formula (IIb) and (IIc) and their complex salts are produced by preferably reacting, for (IIb), diethylenetriamine (III) (product available on the market), while for (IIc), 1,4,7,10-tetraazacyclododecane (IV), synthesized according to known methods (Atkins et al., J.A.C.S., 96, 2268, 1974) [(III) and (IV) are referred to, from now on, as D]

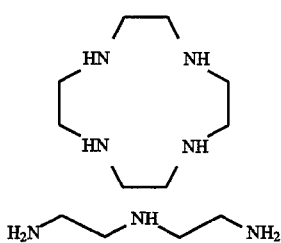

with the desired halo-derivative (V)

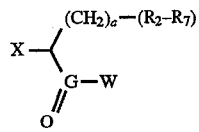

where X=halogen and G, $R_2$–$R_7$, W, a, are as above defined, in order to produce the addition product (VI)

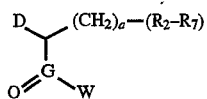

or the corresponding products of polysubstitution on the nitrogen atoms of the macrocycle compound according to the excess of (V) which is used.

On the other hand (VI) or their analogous polysubstitutes to nitrogen can be condensed with the suitable α-halo-acetic derivative (VII), or with a suitable precursor (such as ester or nitrile),

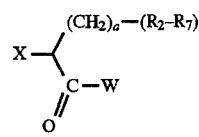

where X=halogen, and $R_2$–$R_7$, W, a, are as above defined, to produce the desired chelating agents of general formula (IIb) and (IIc).

The chelation of the desired metal ion is preferably performed by reacting the suitable derivative of formula (IIb) and/or (IIc) with the stoichiometric amount of metal, in the form of salt or oxide, possibly when the amount of the base or the acid necessary for the neutralization is present.

The condensation between (III) and/or (IV) with (V) is preferably performed in water or chloroform ($CHCl_3$) or in a dipolar aprotic solvent such as di-methylformamide (DMF) or dimethylacetamide (DMA) or acetonitrile ($CH_3CN$), or in a mixture of the same, at a temperature ranging between 30° and 50° C., preferably between 40°–100° C.

The successive condensation between (VI) and (VII) can be performed in aqueous environment or in an organic solvent in the presence of a suitable inorganic or organic base such as sodium hydroxide potassium hydroxide, potassium carbonate or, for example, tetrabutylammonium hydroxide (TBAOH) at a pH value ranging from 8 to 12, preferably 9–11. The temperature can range from 20° to 100° C., preferably 20°–70° C.

The formation of metal complex salts is preferably carried out in water or in an adequate water-alcohol mixture, while the temperature can range from 25° to 100° C., preferably from 40° to 80° C.

The choice of the metal ion and the possible neutralising ion is strictly connected to the use of the complex to be produced.

A non-limiting list of preferred compounds of this invention (disclosed in the experimental part) is hereunder presented, to better emphasise the potential applications of this invention.

GENERAL FORMULA

Compound 1 (Example 1)

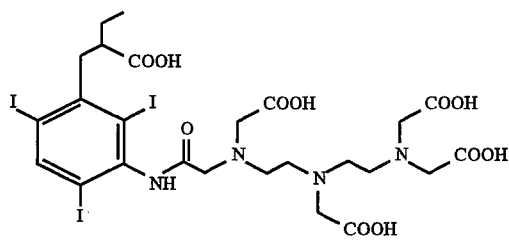

Compound 2 (Example 2)

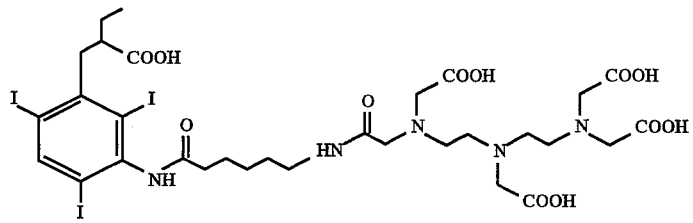

-continued
GENERAL FORMULA
Compound 3 (Example 3)
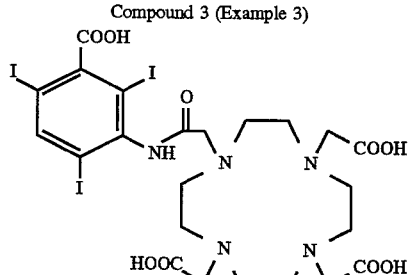
Compound 4 (Example 4)
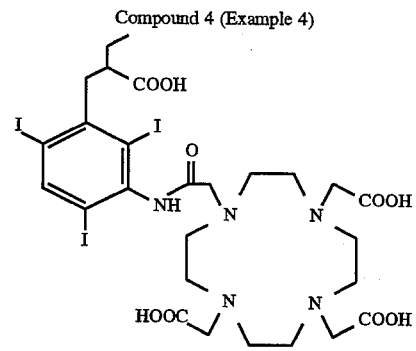
Compound 5 (Example 5)
Compound 6 (Example 6)
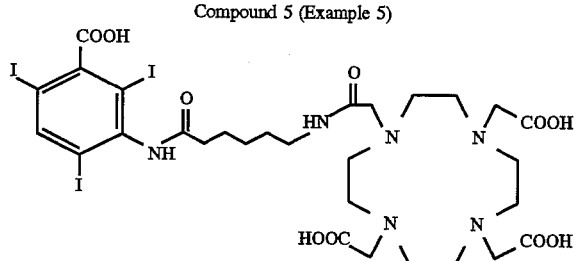
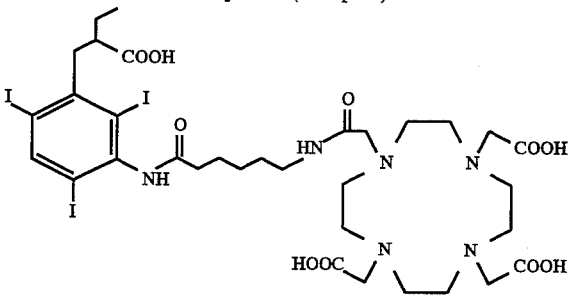
Compound 7 (Example 3)
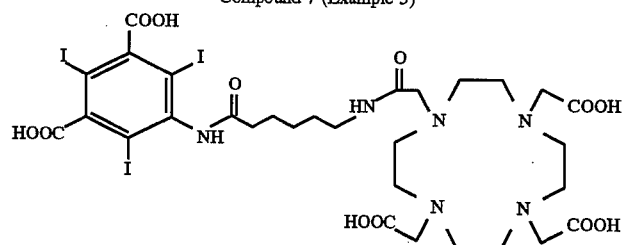
Compound 8 (Example 1)
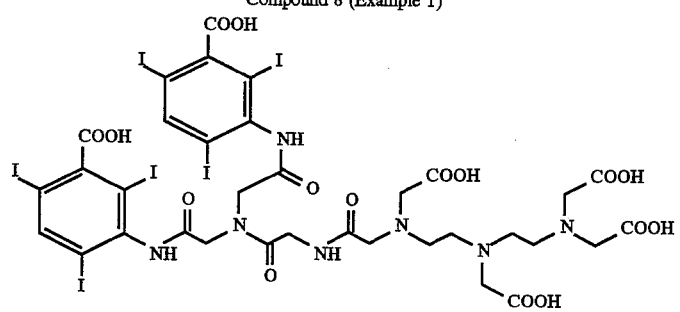
Compound 9 (Example 2)
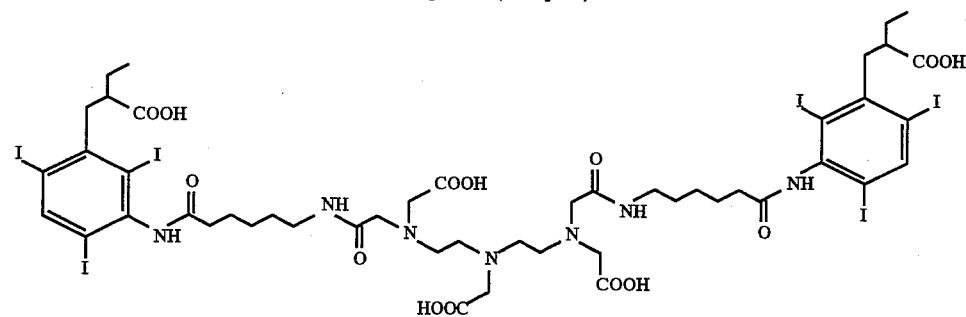

-continued
GENERAL FORMULA

Compound 10 (Example 7)

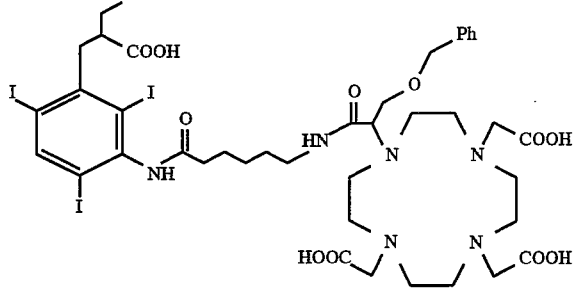

Compound 11 (Example 7)

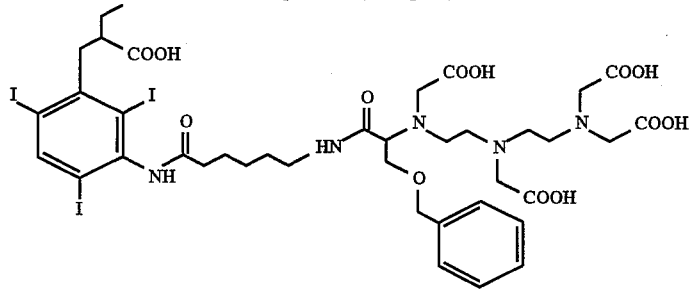

Compound 12 (Example 8)

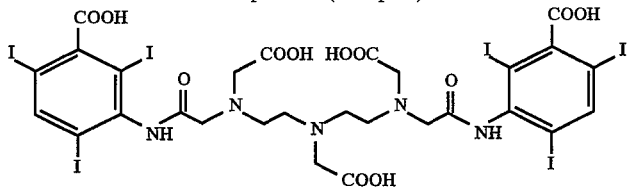

The compounds disclosed in the experimental section also include complex salts of the above mentioned chelating agents with the , following metal cations: $Gd^{(3+)}$, $Yb^{(3+)}$, $La^{(3+)}$ and the neutralizing agents preferably selected were both N-methylglucamine and the sodium ion.

It is intended that all the matter contained in the following section shall be interpreted as illustrative and not in a limiting sense.

EXAMPLE 1

Gadolinium complex of N-[2-[bis(carboxymethyl)amino] ethyl]-N-[2-[[2-[[3-(2-carboxybutyl)-2,4,6-triiodophenyl] amino]-2-oxoethyl](carboxymethyl)amino]ethyl]glycine salified with 1-deoxy-1-(methylamino)-D-glucitol (N-methylglucamine) (1:2)

A) 3-[(2-chloroacetyl)amino]-α-ethyl-2,4,6-triiodobenzenepropanoic acid

To a solution of 50 g of 3-amino-α-ethyl-2,4,6-triiodobenzenepropanoic acid (CAS RN, 96-83-3) (0.0875 mol) in 200 ml of DMA at 0° C., 11.87 g of chloroacetyl chloride (0.10 mol) are added. After 60 minutes at room temperature, the solution is dropwise added to 100 ml of $H_2O$ to give a precipitate which is filtered. The residue is dissolved in 100 ml of $H_2O$ and 43.7 ml of 2N NaOH (0.0875 mol) are added. 42 ml of 2N HCl (0.0084 mol) are added to precipitate a solid which is filtered. 5.4 g of 3-[(2-chloroacetyl)amino]-α-ethyl-2,4,6-triiodobenzenepropanoic acid are obtained (0.083 mol).

Yield: 95.3% m.p.: 157° C. (sint.). K.F.<0.1% (w/w).

| | Elemental analysis | | | | |
|---|---|---|---|---|---|
| | C | H | Cl | I | N |
| % calc.: | 24.11 | 2.03 | 5.47 | 58.80 | 2.16 |
| % found: | 24.31 | 2.11 | 5.43 | 58.48 | 2.13 |

TLC: silica gel plate 60F 254 Merck. Eluent: $CHCl_3$: MeOH: $NH_4OH$ 25%=6:3:1. Detector: UV light (254 nm) Rf=0.65. $^1$H-NMR, $^{13}$C-NMR, IR and MS spectra are consistent with the assigned structure.

B) 3-[[[2-[(2-aminoethyl)amino]ethyl]amino]acetylamino]-α-ethyl-2,4,6-triiodobenzenepropanoic acid To 217 g of diethylenetriamine (product commercially available) (2.1 mol), under stirring and under nitrogen atmosphere, 259 g of compound (A) 3-[(2-chloroacetyl) amino]-α-ethyl-2,4,6-triiodobenzenepropanoic acid (0.40 mol) are added. The mixture is kept at 50° C. for 3 h and, after cooling, is extracted with three 500-ml portions of $CH_2Cl_2$. After evaporation of the solvent, the residue is dissolved in 500 ml of $H_2O$ and acidified with 300 ml of 37% HCl. The resulting solution is counterflow extracted according to Craig with n-BuOH. A residue is obtained, which is purified as trihydrochloride by crystallisation in abs. EtOH after addition of 37% HCl. 187 g of 3-[[[2-[(2-aminoethyl)amino]ethyl]amino]acetylamino]-α-ethyl-2,4, 6-triiodobenzenepropanoic acid (0.227 mol) are obtained.

Yield: 57 % m.p.: 185° C. K.F.: 1.41% (w/w). AgNO$_3$: 99.7% (w/w).

| Elemental analysis | | | | | | |
|---|---|---|---|---|---|---|
| | C | H | Cl | I | N | |
| % calc.: | 24.80 | 3.43 | 12.92 | 46.23 | 6.80 | |
| % found: | 24.92 | 3.45 | 12.81 | 46.34 | 6.70 | H$_2$O 1.41 |

TLC: silica gel plate 60F 254 Merck. Eluent: n-PrOH: NH$_4$OH 25%=7:3. Detector: Cl$_2$Rf=0.25.

$^1$H-NMR, 13C-NMR, IR and MS spectra are consistent with the assigned structure.

C) N-[2-[bis (carboxymethyl)amino]ethyl]-N-[2-[[2-[[3-(2-carboxybutyl)-2,4,6-triiodophenyl]amino]-2-oxo-ethyl ](carboxymethyl)amino]ethyl]glycine A solution of 164.6 g of compound (B) 3-[[[2-[(2-aminoethyl)amino]ethyl]amino]acetylamino]-α-ethyl-2,4,6-triiodobenzenepropanoic acid trihydrochloride (0.20 mol) in 400 ml of H$_2$O, adjusted to pH 10 with 68.4 ml of 10N NaOH (0.684 mol), is dropwise added to a solution of 140 g of bromoacetic acid (product commercially available) (1.0 mol) in 200 ml of H$_2$O. 62.3 ml of 10N NaOH (0.623 mol) are added to the solution to keep pH value of 10. The reaction mixture is stirred for 20 h at room temperature. The solution is acidified directly with conc. (374) HCl at pH 2.4 obtaining a precipitate which is purified by preparative HPLC. After evaporation of the solvent, 63.5 g of N-[2-[bis (carboxymethyl)amino]ethyl]-N-[2-[[2-[[3-(2-carboxybutyl)- 2,4,6-triiodophenyl]amino]-2-oxoethyl] (carboxymethyl)amino]ethyl]glycine (0.067 mol) are obtained.

Yield: 33% m.p.: 120° C. (sint); 140° C. (dec). Acidimetric assay (0.1N NaOH): 94.0% (w/w). Complexometric assay (0.1N ZnSO$_4$): 91.6% (w/w). HPLC: 96.0% (in area %). Column: E. Merck Lichrospher 100 RP-8; mm 250×4 mm; Mobile phase: A=aqueous solution of H$_3$PO$_4$ 0.017M and KH$_2$PO$_4$ 0.01M; B=CH$_3$CN; Flow: 1 ml min$^{-1}$; Temperature: 40° C.; Detection: UV LIGHT 210 nm.

| Elemental analysis | | | | |
|---|---|---|---|---|
| | C | H | I | N |
| % calc.: | 31.73 | 3.52 | 40.23 | 5.92 |
| % found: | 31.85 | 3.63 | 39.99 | 6.00 |

$^1$H-NMR, $^{13}$C-NMR, IR and MS spectra are consistent with the assigned structure.

D) Gadolinium complex of N-[2-[bis(carboxymethyl) amino]ethyl]-N-[2-[[2-[[3-(2-carboxybutyl)-2,4,6-triiodophenyl]amino]-2-oxoethyl](carboxymethyl)amino] ethyl]glycine salified with 1-deoxy-1-(methyl-amino)-D-glucitol (N-methylglucamine) (1:2)

30.8 g of compound (C) N-[2-[bis(carboxymethyl)amino] ethyl]-N-[2-[[2-[[3-(2-carboxybutyl)-2,4,6-triiodophenyl] amino]-2-oxoethyl](carboxymethyl)amino]ethyl]glycine (0.03 mol) are dissolved in 300 ml of H$_2$O and adjusting the pH to 6.5 with 95 ml of 1N N-methylglucamine (0.095 mol). A solution of 11.5 g of GdCl$_3$.6H$_2$O (0.03 mol) is dropwise added to 150 ml of H$_2$O keeping the pH at 6.5 by addition of 1N N-methylglucamine (total 152 ml, 0.152 mol), obtaining a solution which is evaporated to dryness. 41.4 g of gadolinium complex of N-[2-[bis (carboxymethyl)amino] ethyl]-N-[2-[[2-[[3-(2-carboxybutyl)-2,4,6-triiodophenyl] amino]-2-oxoethyl](carboxymethyl)amino]ethyl]glycine salified with 1-deoxy-1-(methylamino)-D-glucitol (N-methylglucamine) (1:2) (0.0273 mol) are obtained.

Yield: 91% m.p.: 178°–180° C. (208° C dec.). K.F.: 1.76% (w/w).

| Elemental analysis | | | | | |
|---|---|---|---|---|---|
| | C | H | Gd | I | N |
| % calc.: | 31.42 | 4.33 | 10.55 | 25.54 | 5.64 |
| % found: | 31.01 | 4.61 | 10.09 | 24.81 | 5.53 |

The following compound was prepared through the same procedure:

gadolinium complex of 3,3'-[[13-carboxy-6,9,12-tris-(carboxymethyl)-1,4-dioxo-3,6,9,12-tetraazatridecyl]-imino-bis[(1-oxo-2,1-ethanediyl)imino]]bis[2,4,6-triiodobenzoic acid] salified with 1-deoxy-1-(methylamino) -D-glucitol (N-methylglucamine) (1:3) (Compound 8).

EXAMPLE 2

Gadolinium complex of 18-[[3-(2-carboxybutyl)-2,4,6-triiodophenyl]amino]-3,6,9-tris(carboxymethyl)-11,18-dioxo-3,6,9,12-tetraazaoctadecanoic acid salified with 1-deoxy-1-(methylamino)-D-glucitol (N-methylglucamine) (1:2)

A) 3-[[6-[(chloroacetyl)amino]-1-oxohexyl]amino]-α-ethyl-2,4,6-triiodobenzenepropanoic acid In a solution of 43.9 g of DMF (0.6 mol) in 700 ml of CH$_2$Cl$_2$, kept at a temperature of 5° C. and under nitrogen atmosphere, 109.2 g of oxalyl chloride (0.86 mol) are dropwise added, obtaining a white precipitate. After 1 h, the solvent and the oxalyl chloride excess are removed under reduced pressure. The residue is suspended in 1000 ml of THF and 500 ml of MeCN and in the suspension kept at a temperature of 5° C., a solution of 130 g of 6-[(chloroacetyl) amino]hexanoic acid (prepared according to the procedure described in J. Chromatography, 1984, 292, 369–382) (0.63 mol) is dropwise added and 47.5 g of pyridine (0.6 mol) in 500 ml of THF. The reaction mixture is then heated to 40° C. for 2 h. A solution of 171.3 g of 3-amino-α-ethyl-2,4,6-triiodobenzenepropanoic acid (CAS RN 96-83-3) (0.30 mol) in 300 ml of THF is slowly added and the whole is heated for 3 h at reflux. The solution is concentrated and the residue is dissolved in 500 ml of H$_2$O. The pH is adjusted to 8 with 620 ml of 2N NaOH (1.24 mol) and THF is evaporated under reduced pressure. The aqueous solution is extracted 3 times with 200 ml portions of CH$_2$Cl$_2$. The organic phases are collected and washed with 200 ml of H$_2$O at pH 8. The aqueous phases are acidified with 200 ml of 37% HCl yielding a precipitate, which is filtered. 181 g of 3-[[6-[(chloroacetyl)amino]-1-oxohexyl]amino]-α-ethyl-2,4,6-triiodobenzenepropanoic acid (0.238 mol) are obtained.

Yield: 79% m.p.: 173° C. (dec.). K.F.: 0.14% (w/w).

| Elemental analysis | | | | | | |
|---|---|---|---|---|---|---|
| | C | H | Cl | I | N | |
| % calc.: | 30.00 | 3.18 | 4.66 | 50.06 | 3.68 | |
| % found: | 30.00 | 3.15 | 4.40 | 40.36 | 3.65 | H$_2$O 0.14 |

$^1$H-NMR, $^{13}$C-NMR, IR and MS spectra are consistent with the assigned structure.

B) 3-[6-[[[2-[(2-aminoethyl)amino]ethyl]amino] acetylamino]-1-oxohexyl]amino-α-ethyl-2,4,6-triiodobenzenepropanoic acid According to the procedure described in Example 1, 123 g of diethylenetriamine (0.16 mol) are reacted with 121.7 g of compound (A) 3-[[6-[(chloroacetyl)amino]-1-oxohexyl]amino]-α-ethyl-2,4,6-triiodobenzene propanoic acid. 64 g of 3-[6-[[[2-[(2-aminoethyl)amino]ethyl]amino]acetyl amino]-1-oxohexyl]amino-α-ethyl-2,4,6-triiodobenzenepropanoic acid (0.077 mol) are obtained.

Yield: 48%. K.F.: 1.00% (w/w). HCl: 97.5% (w/w).

| | Elemental analysis | | | |
|---|---|---|---|---|
| | C | H | I | N |
| % calc.: | 33.39 | 4.39 | 46.02 | 8.46 |
| % found: | 33.67 | 4.40 | 45.43 | 8.36 | H$_2$O 1.00 |

TLC: silica gel plate 60F 254 Merck. Eluent: nPrOH: NH$_4$OH 25%=7:3. Detector: Cl$_2$ and starch indicator/KI Rf=0.46. $^1$H-NMR, $^{13}$C-NMR, IR and MS spectra are consistent with the assigned structure.

C) 18-[[3-(2-carboxybutyl)-2,4,6-triiodophenyl]amino]-3,6,9-tris(carboxymethyl)-11,18-dioxo-3,6,9,12-tetraazaoctadecanoic acid According to the procedure described in Example 1, 52.1 g of bromoacetic acid (0.375 mol) are reacted with 62 g of compound (B) 3-[6- [[[2-[(aminoethyl)amino]ethyl]amino]acetylamino]-1-oxohexyl]amino-α-ethyl-2,4,6-triiodobenzenepropanoic acid (0.075 mol) in 400 ml of H$_2$O. 32.9 g of 18-[[3-(2-carboxybutyl)-2,4,6-triiodophenyl]amino]-3,6,9-tris(carboxymethyl)-11,18-dioxo-3,6,9,12-tetraazaoctadecanoic acid (0.031 mol) are obtained.

Yield: 41% .m.p.: 138° C. (dec). Acidimetric assay (0.1N NaOH): 95.2% (w/w). Complexometric assay (0.1N ZnSO$_4$): 93.8% (w/w). HPLC: 97.0% (% in area).

| | Elemental analysis | | | |
|---|---|---|---|---|
| | C | H | I | N |
| % calc.: | 35.15 | 4.19 | 35.94 | 6.61 |
| % found: | 35.34 | 4.45 | 35.35 | 6.78 |

$^1$H-NMR, $^{13}$C-NMR, IR and MS spectra are consistent with the assigned structure.

D) Gadolinium complex of 18-[[3-(2-carboxybutyl)-2,4,6-triiodophenyl]amino]-3,6,9-tris(carboxymethyl)-11,18-dioxo-3,6,9,12-tetraazaoctadecanoic acid salified with 1-deoxy-1-(methylamino)-D-glucitol (N-methytglucamine) (1:2)

According to the procedure described in Example 1, 15.7 g of compound (C) 18-[[3-(2-carboxybutyl)-2,4,6-triiodophenyl]amino]-3,6,9-tris(carboxymethyl)-11,18-dioxo-3,6,9,12-tetraazaoctadecanoic acid (0.014 mol) are dissolved in 100 ml of H$_2$O and reacted with 5.2 g of GdCl$_3$.6H$_2$O (0.014. mol) and 70.55 ml of 1N N-methylglucamine (0.071 mol). 16.8 g of the gadolinium complex are obtained (0.010 mol).

Yield: 74% m.p.: 167° C. (dec). K.F.: 1.28% (w/w). HPLC: 96.4% (in area %). Free chelating agent: 0.09% (w/w).

| | Elemental analysis | | | | |
|---|---|---|---|---|---|
| | C | H | Gd | I | N |
| % calc.: | 33.66 | 4.71 | 9.80 | 23.73 | 6.11 |
| % found: | 33.25 | 4.99 | 9.44 | 22.81 | 5.95 | H$_2$O 1.28 |

The following compound was prepared according to the same procedure:
gadolinium complex of [(carboxymethyl)iminobis[[[(2,1-ethanediyl)(carboxymethyl)imino](1-oxo-2,1-ethanediyl)imino(1-oxo-6,1-hexanediyl)imino]]bis[α-ethyl-2,4,6-triiodobenzenepropanoic acid] salified with 1-deoxy-1-(methylamino)-D-glucitol (N-methylglucamine) (1:2) (Compound 9).

EXAMPLE 3

Gadolinium complex of 10-[2-[(3-carboxy-2,4,6-triiodophenylamino]-2-oxoethyl]-1,4,7,10-tetraazacyclododecane-1,4,7-triacetic acid salified with 1-deoxy-1-(methylamino)-D-glucitol (N-methylglucamine) (1:1)

A) 3-[(2-chloroacetyl)amino]-2,4,6-triiodobenzoic acid

According to the procedure described in Example 1, a suspension of 103 g of 3-amino-2,4,6-triiodobenzoic acid (Beil. XIV, 414) (0.2 mol) in 200 ml of DMA is added to 24.8 g of chloroacetyl chloride (0.22 mol). 93.27 g of 3-[(2-chloroacetyl)amino]-2,4,6-triiodobenzoic acid are obtained (0.158 mol).

Yield: 79% m.p.: 253°–255° C.

| | Elemental analysis | | | | |
|---|---|---|---|---|---|
| | C | H | Cl | I | N |
| % calc.: | 18.28 | 0.85 | 5.99 | 64.38 | 2.37 |
| % found: | 18.32 | 0.83 | 5.79 | 64.62 | 2.35 |

TLC: silica gel plate 60F 254 Merck. Eluent: CHCl$_3$: MeOH: NH$_4$OH 25%=4:4:2. Detector: UV light (254 nm) Rf=0.69. $^1$H-NMR, $^{13}$C-NMR, IR and MS spectra are consistent with the assigned structure.

B) N-(3-carboxy-2,4,6-triiodophenyl)-1,4,7,10-tetraazacyclododecane-1-acetamide

To a solution of 143.9 g of 1,4,7,10-tetraazacyclododecane (product commercially available) (0.84 mol) in 1000 ml of CH$_3$CN under reflux, a suspension of 50 g of compound (A) 3-[(2-chloro-1-oxoethyl)amino]-2,4,6-triiodobenzoic acid (0.084 mol) in 500 ml of CH$_3$CN is added during 1 h. The mixture is kept under reflux for 24 h, yielding a solid precipitation. The reaction mixture is filtered and the solid is purified by chromatography on silica gel. 55 g of N-(3-carboxy-2,4,6-triiodophenyl)-1,4,7,10-tetraazacyclododecane-1-acetamide (0.076 mol) are obtained.

Yield: 90% m.p.: 245°–246° C. K.F.: 1.83% (w/w).

| | Elemental analysis | | | |
|---|---|---|---|---|
| | C | H | I | N |
| % calc.: | 28.07 | 3.33 | 52.35 | 9.63 |
| % found: | 27.35 | 3.38 | 50.79 | 9.23 | H$_2$O 1.83 |

TLC: silica gel plate 60F 254 Merck. Eluent: CHCl$_3$: MeOH: NH$_4$OH 25%=6:3:1. Detector: UV light (254 nm)

Rf=0.20. $^{1}$H NMR $^{13}$C-NMR, IR and MS spectra are consistent with the assigned structure.

C) 10-[2-[(3-carboxy-2,4,6-triiodophenyl)amino]-2-oxoethyl]-1,4,7,10-tetraazacyclododecane-1,4,7-triacetic acid 18.9 g of bromoacetic acid (product available on the market) (0.136 mol) are dissolved in 20 ml of H$_2$O, and by keeping the temperature below 10° C., the solution pH is adjusted to 5 with 68 ml of 2N NaOH (0.136 mol). After adding a solution of 30 g of compound. (B) N-(3-carboxy-2,4,6-triiodophenyl)-1,4,7,10-tetraazacyclododecane-1-acetamide (0.041 mol) in 20.5 ml of 2N NaOH, the reaction mixture is heated at 50° C. for 15 h keeping the pH at 10 with 6.15 ml of 2N NaOH (0.123 mol). A solid precipitates which is then filtered and dissolved in 200 ml of H$_2$O. After acidification of the solution with 82 ml of HCl 2N (0.164 mol) the precipitate is filtered. 28.2 g of 10-[2-[(3-carboxy-2,4,6-triiodophenyl)amino]-2-oxoethyl]-1,4,7,10-tetraazacyclododecane-1,4,7-triacetic acid (0.029 mol) are obtained.

Yield: 71% m.p.: 235° C. K.F.: 6.16% (w/w).

| Elemental analysis | | | | | |
|---|---|---|---|---|---|
| | C | H | I | N | |
| % calc.: | 30.65 | 3.36 | 42.24 | 7.77 | |
| % found: | 28.04 | 3.63 | 39.32 | 7.03 | H$_2$O 6.16 |

$^{1}$H-NMR, $^{13}$C-NMR, IR and MS spectra are consistent with the assigned structure.

D) Gadolinium complex of 10-[2-[(3-carboxy-2,4,6-triiodophenylamino]-2-oxoethyl]-1,4,7,10-tetraazacyclododecane-1,4,7-triacetic acid salified with 1-deoxy-1-(methylamino)-D-glucitol (N-methylglucamine) (1:1)

To a suspension of 23.19 g of compound (C) 10-[2-[(3-carboxy-2,4,6-triiodophenyl)amino]-2-oxoethyl]-1,4,7,10-tetraazacyclododecane-1,4,7-triacetic acid (0.026 mol) in 2300 ml of H$_2$O, 4.88 g of N-methylglucamine (product commercially available) (0.025 mol) and 4.66 g of Gd$_2$O$_3$ (product available on the market) (0.013 mol) are added. The mixture is heated at 50° C. for 20 h producing a complete solubilization. After cooling, the pH is adjusted to 7 with 0.195 g of N-methylglucamine (0.001 mol). The reaction mixture is filtered and the filtrate is evaporated to dryness. 35.4 g of gadolinium complex of 10-[2-[(3-carboxy-2,4,6-triiodophenylamino]-2-oxoethyl]-1,4,7,10-tetraazacyclododecane-1,4,7-triacetic acid salified with 1-deoxy-1-(methylamino)-D-glucitol (N-methylglucamine) (1:1) (0.026 mol) are obtained.

Yield: quantitative m.p.: >280° C. HPLC: 100% (% in area). K.F.: 8.254 (w/w).

| Elemental analysis | | | | | | |
|---|---|---|---|---|---|---|
| | C | H | Cl | I | N | |
| % calc.: | 28.80 | 3.55 | 12.57 | 30.43 | 6.72 | |
| % found: | 26.75 | 4.30 | 11.25 | 27.33 | 6.13 | H$_2$O 8.25 |

The following compound was prepared according to the same procedure:
gadolinium complex of 3-[[6-[[[4,7,10-tris(carboxymethyl)-1,4,7,10-tetraazacyclododec-1-yl]acetyl]amino]-1-oxohexyl]amino]-2,4,6-triiodo-1,3-benzenedicarboxylic acid salified with 1-deoxy-1-(methylamino)-D-glucitol (N-methylglucamine) (1:2) (Compound 7).

EXAMPLE 4

Lanthanides complexes (Gd$^{+3}$,Yb$^{+3}$,La$^{+3}$) of 10-[2-[[3-(2-carboxybutyl)-2,4,6-triiodophenyl]amino]-2-oxoethyl]-1,4,7,10-tetraazacyclododecane-1,4,7-triacetic acid salified with sodium or 1-deoxy-1-(methylamino)-D-glucitol (N-methylglucamine) (1:1)

A) N-[3-(2-carboxybutyl)-2,4,6-triiodophenyl]-1,4,7,10-tetraazacyclododecane-1-acetamide According to the procedure described in Example 3, 105.8 g of 1,4,7,10-tetraazacyclododecane (0.62 mol) in 600 ml of CH$_3$CN are added to a suspension of 40 g of 3-[(2-chloro-1-oxoethyl)amino]-α-ethyl-2,4,6-triiodobenzenepropanoic acid (prepared as described in Example 1) (0.62 mol) in 500 ml of CH$_3$CN. 35.8 g of N-[3-(2-carboxybutyl)-2,4,6-triiodophenyl]-1,4,7,10-tetraazacyclododecane-1-acetamide (0.046 mol) are obtained.

Yield: 75% m.p.: 201° C. K.F.: 7.22 (w/w).

| Elemental analysis | | | | | |
|---|---|---|---|---|---|
| | C | H | I | N | |
| % calc.: | 32.20 | 4.12 | 48.61 | 8.94 | |
| % found: | 29.64 | 4.46 | 45.16 | 8.36 | H$_2$O 7.22 |

TLC: silica gel plate 60F 254 Merck. Eluent: CHCl$_3$: MeOH: NH$_4$OH 25%=6:3:1. Detector: UV light (254 nm) Rf=0.30. $^{1}$H-NMR, $^{13}$C-NMR, IR and MS spectra are consistent with the assigned structure.

B) 10-[2-[[3-(2-carboxybutyl)-2,4,6-triiodophenyl]amino]-2-oxoethyl]-1,4,7,10-tetraazacyclododecane-1,4,7-triacetic acid According to the procedure described in Example 3, 17.74 g of bromoacetic acid (0.127 mol) in 20 ml of H$_2$O are reacted with 25 g of compound (B) N-[3-(2-carboxybutyl)-2,4,6-triiodophenyl]-1,4,7,10-tetraazacyclododecane-1-acetamide (0.032 mol) in 20 ml of H$_2$O. 4.1 g of 10-[2-[[3-(2-carboxybutyl)-2,4,6-triiodophenyl]amino]-2-oxoethyl ]-1,4,7,10-tetraazacyclododecane-1,4,7-triacetic acid (0.0043 mol) are obtained.

Yield: 13% m.p.: 230° C. K.F.: 3.02 % (w/w).

| Elemental analysis | | | | | |
|---|---|---|---|---|---|
| | C | H | I | N | |
| % calc.: | 33.86 | 4.00 | 39.76 | 7.32 | |
| % found: | 33.10 | 4.20 | 37.74 | 7.11 | H$_2$O 3.02 |

TLC: silica gel plate 60F 254 Merck. Eluent: CHCl$_3$: MeOH: NH$_4$OH 25%=6:3:1. Detector: UV light (254 nm) Rf=0.25. $^{1}$H-NMR, $^{13}$C-NMR, IR and MS spectra are consistent with the assigned structure.

C) Lanthanides complexes (Gd$^{+3}$,Yb$^{+3}$,La$^{+3}$) of 10-[2-[[3-(2-carboxybutyl)-2,4,6-triiodophenyl]amino]-2-oxoethyl]-1,4,7,10-tetraazacyclododecane-1,4,7-triacetic acid 5.1 g of compound (B) 10-[2-[[3-(2-carboxybutyl)-2,4,6-triiodophenyl]amino]-2-oxoethyl]-1,4,7,10-tetraazacyclododecane-1,4,7-triacetic acid (0.005 mol) are suspended in 50 ml of H$_2$O and dissolved by adding 2N NaOH to pH 6.5. A solution of the desired metal chloride is dropwise added to 10 ml of H$_2$O by keeping the pH at 6.5 with 12.8 ml of 2N NaOH (0.0064 mol). The solution is acidified with HCl (18%) at pH 2 and by germination, a precipitate is formed which is filtered. Yields and analytical data are hereunder reported.

Gadolinium complex of 10-[2-[[3-(2-carboxybutyl)-2,4,6-triiodophenyl]amino]-2-oxoethyl]-1,4,7,10-tetraazacyclododecane-1,4,7-triacetic acid Yield: 85% m.p.: >250° C. HPLC: 97% (% in area). K.F.: 2.75% (w/w).

Elemental analysis

|  | C | H | Gd | I | N |  |
|---|---|---|---|---|---|---|
| % calc.: | 29.18 | 3.17 | 14.15 | 34.25 | 6.30 |  |
| % found: | 27.81 | 3.49 | 13.56 | 32.36 | 5.93 | $H_2O$ 2.75 |

Ytterbium complex of 10-[2-[[3-(2-carboxybutyl)-2,4,6-triiodophenyl]amino]-2-oxoethyl]-1,4,7,10-tetraazacyclododecane-1,4,7-triacetic acid Yield: 71% m.p.: >250° C. HPLC: 97.4% (% in area). K.F.: 1.55% (w/w).

Elemental analysis

|  | C | H | I | N | Yb |  |
|---|---|---|---|---|---|---|
| % calc.: | 28.77 | 3.13 | 33.77 | 6.21 | 15.35 |  |
| % found: | 27.51 | 3.48 | 33.36 | 5.89 | 15.15 | $H_2O$ 1.55 |

Lanthanum complex of 10-[2-[[3-(2-carboxybutyl)-2,4,6-triiodophenyl]amino]-2-oxoethyl]-1,4,7,10-tetraazacyclododecane-1,4,7-triacetic acid Yield: 57% m.p.: >250 ° C. HPLC: 96.0% (in area %). K.F.: 2.95% (w/w).

Elemental analysis

|  | C | H | I | La | N |  |
|---|---|---|---|---|---|---|
| % calc.: | 29.66 | 3.23 | 34.82 | 12.70 | 6.41 |  |
| % found: | 29.28 | 3.34 | 32.83 | 12.66 | 5.89 | $H_2O$ 2.95 |

D) Lanthanides complexes ($Gd^{+3}$, $Yb^{+3}$, $La^{+3}$) of 10-[2-[[3-(2-carboxybutyl)-2,4,6-triiodophenyl]amino]-2-oxoethyl]-1,4,7-triacetic acid salified with sodium (1:1)

A suspension of complexes (C), as above described, is adjusted to pH 7 with 2N NaOH in 30 ml of $H_2O$, producing a solution which is evaporated to dryness to give the desired product. Yields and analytical data are hereunder reported.

Gadolinium complex of 10-[2-[[3-(2-carboxybutyl)-2,4,6-triiodophenyl]amino]-2-oxoethyl]-1,4,7,10-tetraazacyclododecane-1,4,7-triacetic acid salified with sodium (1:1).

Yield: 100% m.p.: >250° C. K.F.: 3.46% (w/w).

Elemental analysis

|  | C | H | Gd | I | N | Na |  |
|---|---|---|---|---|---|---|---|
| % calc.: | 28.61 | 3.02 | 13.87 | 33.59 | 6.38 | 2.03 |  |
| % found: | 27.86 | 3.34 | 13.40 | 32.60 | 5.94 | 1.95 | $H_2O$ 3.46 |

Ytterbium complex of 10-[2-[[3-(2-carboxybutyl)-2,4,6-triiodophenyl]amino]-2-oxoethyl]-1,4,7,10-tetraazacyclododecane-1,4,7-triacetic acid salified with sodium (1:1).

Yield: 81% m.p.: >250° C. K.F.: 1.60% (w/w).

Elemental analysis

|  | C | H | I | N | Na | Yb |
|---|---|---|---|---|---|---|
| % calc.: | 28.22 | 2.98 | 33.12 | 6.09 | 2.00 | 15.06 |
| % found: | 27.73 | 3.36 | 32.57 | 5.89 | 1.97 | 14.64 |

Lanthanum complex of 10-[2-[[3-(2-carboxybutyl)-2,4,6-triiodophenyl]amino]-2-oxoethyl]-1,4,7,10-tetraazacyclododecane-1,4,7-triacetic acid salified with sodium (1:1).

Yield: 58% m.p.: >250° C. K.F.: 2.04% (w/w).

Elemental analysis

|  | C | H | I | La | N | Na |  |
|---|---|---|---|---|---|---|---|
| % calc.: | 29.08 | 3.07 | 34.14 | 12.46 | 6.09 | 2.00 |  |
| % found: | 28.17 | 3.53 | 32.99 | 11.94 | 6.01 | 2.24 | $H_2O$ 2.04 |

E) Gadolinium complex of 10-[2-[[3-(2-carboxybutyl)-2,4,6-triiodophenyl]amino]-2-oxoethyl]-1,4,7,10-tetraazacyclododecane-1,4,7-triacetic acid salified with 1-deoxy-1-(methylamino)-D-glucitol (N-methylglucamine) (1:1)

A suspension of 47.9 g of compound (C) gadolinium complex of 10-[2-[[3-(2-carboxybutyl)-2,4,6-triiodophenyl]amino]-2-oxoethyl]-1,4,7,10-tetraazacyclododecane-1,4,7-triacetic acid (0.042 mol) in 100 ml of $H_2O$, is adjusted to pH 6.5 with 8.2 g of N-methylglucamine (0.042 mol) yielding a solution which is evaporated to dryness. 53.6 g of gadolinium complex of 10-[2-[[3-(2-carboxybutyl)-2,4,6-triiodophenyl]amino]-2-oxoethyl]-1,4,7,10-tetraazacyclododecane-1,4,7-triacetic acid salified with 1-deoxy-1-(methylamino)-D-glucitol(N-methylglucamine) (1:1) (0.041 mol) are obtained.

Yield: 83% m.p.: >250° C. HPLC: 96.9% (% in area). K.F.: 1.92% (w/w).

Elemental analysis

|  | C | H | Gd | I | N |  |
|---|---|---|---|---|---|---|
| % calc.: | 31.25 | 4.01 | 12.03 | 29.13 | 6.34 |  |
| % found: | 30.75 | 4.18 | 11.94 | 28.54 | 6.29 | $H_2O$ 1.92 |

EXAMPLE 5

Gadolinium complex of 3-[[6-[[[4,7,10-tris (carboxymethyl)-1,4,7,10-tetraazacyclododec-1-yl]acetyl]amino]-1-oxohexyl]amino]-2,4,6-triiodobenzoic acid salified with 1-deoxy-1(methylamino)-D-glucitol (N-methylglucamine) (1:1)

A) 3-[6-[(chloroacetyl)amino]-1-oxohexyl]amino-2,4,6-triiodobenzoic acid

To 207.6 g of 6-[(chloroacetyl)amino]hexanoic acid (prepared according to the procedure described in J. Chromatography 1984, 292, 369–382) (1.00 mol), 305.4 g of thionyl chloride (2.57 mol) are slowly added and the reaction mixture heated at 60° C. After 3 h, the thionyl chloride in excess is removed. The residue is dropwise added to a suspension of 360.7 g of 3-amino-2,4,6-triiodobenzoic acid (Beil. XIV, 414) (0.70 mol) in 600 ml of DMA, and leaving the temperature to rise up to 55° C. The temperature is adjusted to 60° C. and maintained for 2 h. The resulting solution is poured in 6 l of H₂O and ice obtaining a precipitate which is filtered. The residue is dissolved in 2 l of methyl ethyl ketone, the solution is concentrated, and after germination, the desired product precipitates. 212.3 g of 3-[6-[(chloroacetyl)amino]-i-oxohexyl]amino-2,4,6-triiodobenzoic acid (0.30 mol) are obtained.

Yield: 43% m.p.: 101° C. AgNO₃ (0.1N): 94.8%. K.F.: 0.53% (w/w).

| Elemental analysis | | | | | |
|---|---|---|---|---|---|
| | C | H | Cl | I | N |
| % calc.: | 25.57 | 2.29 | 5.03 | 54.03 | 3.98 |
| % found: | 25.40 | 2.23 | 5.10 | 54.40 | 3.90 H₂O 0.53 |

¹H-NMR, ¹³C-NMR, IR and MS spectra are consistent with the assigned structure.

B) 3-[[1-oxo-6-[[(1,4,7,10-tetraazacyclododec-1-yl) acetyl] amino]hexyl]amino]-2,4,6-triiodobenzoic acid trihydrochloride To a solution of 171.3 g of 1,4,7,10-tetraazacyclododecane (1.00 mol) in 500 ml of DMA, a solution of 176.14 g of compound (A) 3-[6-[(chloroacetyl) amino]-1-oxohexyl]amino-2,4,6-triiodobenzoic acid (0.25 mol) is added to 250 ml of DMA. After 30 minutes, the solution is concentrated and the residue is diluted with 600 ml of H₂O. The resulting aqueous solution is acidified with 37% HCl and saturated with n-BuOH and counterflow extracted according to Craig's method with n-BuOH saturated with H₂O and H₂O saturated with n-BuOH. The organic phases are evaporated to dryness. The residue is dissolved in 2000 ml of abs. EtOH and 200 ml of 5N HCl in abs. EtOH are added, obtaining a precipitate which is filtered.

155.5 g of 3-[[1-oxo-6-[[(1,4,7,10-tetraazacyclododec-1-yl) acetyl]amino]hexyl]amino]-2,4,6-triiodobenzoic acid trihydrochloride (0.164 mol) are obtained.

Yield: 65% m.p.: 210° C. AgNO₃ (0.1N): 94.8%. K.F.: 1.58% (w/w).

| Elemental analysis | | | | | |
|---|---|---|---|---|---|
| | C | H | Cl | I | N |
| % calc.: | 29.09 | 4.03 | 11.20 | 40.09 | 8.85 |
| % found: | 29.51 | 4.04 | 10.59 | 39.20 | 8.60 H₂O 1.58 |

¹H-NMR, ¹³C-NMR, IR and MS spectra are consistent with the assigned structure.

C) 3-[[6-[[[4,7,10-tris(carboxymethyl)-1,4,7,10-tetraazacyclododec-1-yl]acetyl]amino]-1-oxohexyl]amino]-2,4,6-triiodobenzoic acid According to the procedure described in Example 3, 142.4 g of compound (B) 3-[[1-oxo-6-[[(1,4,7,10-tetraazacyclododec-1-yl) acetyl]amino]hexyl]amino]-2,4,6-triiodobenzoic acid trihydrochloride (0.15 mol ) are reacted with 83.4 g of bromoacetic acid (0.60 mol) in 750 ml of 96% EtOH and 250 ml of H₂O. 72.7 g of 3-[[6-[[[4,7,10-tris (carboxymethyl)-1,4,7,10-tetraazacyclododec-1-yl]acetyl] amino]-1-oxohexyl]amino]-2,4,6-triiodobenzoic acid (0.072 mol) are obtained.

Yield: 48% m.p.: 230° C. (dec.). Complexometric assay (0.1N ZnSO₄): 95.4%. K.F.: 1.23% (w/w).

| Elemental analysis | | | | |
|---|---|---|---|---|
| | C | H | I | N |
| % calc.: | 34.34 | 4.07 | 37.53 | 8.28 |
| % found: | 34.00 | 4.13 | 37.29 | 8.17 H₂O 1.23 |

¹H-NMR, ¹³C-NMR, IR and MS spectra are consistent with the assigned structure.

D) Gadolinium complex of 3-[[6-[[[4,7,10-tris (carboxymethyl)-1,4,7,10-tetraazacyclododec-1-yl]acetyl] amino]-1-oxohexyl]amino]-2,4,6-triiodobenzoic acid salified with 1-deoxy-1-(methylamino)-D-glucitol (1:1)

According to the procedure described in Example 1, 45.8 g of compound (C) 3-[[6-[[[4,7,10-tris(carboxymethyl)-1,4, 7,10-tetraazacyclododec-1-yl]acetyl]amino]-1-oxohexyl] amino]-2,4,6-triiodobenzoic acid (0.04 mol) in 400 ml of H₂O are reacted with 14.9 g of GdCl₃.6H₂O (0.04 mol) and 163 ml of an aqueous solution of 1N N-methylglucamine (0.163 mol). 46.7 g of gadolinium complex of 3-[[6-[[[4,7, 10-tris(carboxymethyl)-1,4,7,10-tetraazacyclododec-1-yl] acetyl]amino]-1-oxohexyl]amino]-2,4,6-triiodobenzoic acid salified with 1-deoxy-1-(methylamino)-D-glucitol (1:1) (0.034 mol) are obtained.

Yield: 86% m.p.: >250° C. K.F.: 3.79%.

| Elemental analysis | | | | | |
|---|---|---|---|---|---|
| | C | H | Gd | I | N |
| % calc.: | 31.70 | 4.06 | 11.53 | 27.91 | 7.19 |
| % found: | 30.80 | 4.55 | 10.65 | 26.57 | 6.92 H₂O 3.79 |

EXAMPLE 6

Gadolinium complex of α-ethyl-2,4,6-triiodo-3-[[1-oxo-6- [[4,7,10-tris(carboxymethyl)-1,4,7,10-tetraazacyclododec-1-yl-acetyl]amino]hexyl]amino] benzenepropanoic acid salified with 1-deoxy-1-(methylamino)-D-glucitol (1:1)

A) α-ethyl-2,4,6-triiodo-3-[[1-oxo-6-[(1,4,7,10-tetraazacyclododec-1-ylacetyl)amino]hexyl]amino] benzenepropanoic acid According to the procedure described in Example 5, 171.3 g of 1,4,7,10-tetraazacyclododecane (1,00 mol) in 500 ml of DMA are reacted with 190 g of 3-[[6-[(chloroacetyl) amino] -1-oxohexyl]amino]-α-ethyl-2,4,6 -triiodobenzenepropanoic acid (prepared according to the procedure described in Example 2) (0,25 mol) in 250 ml of DMA. 155 g of α-ethyl-2,4,6-triiodo-3-[[1-oxo-6-[(1,4,7, 10-tetraazacyclododec-1-yl-acetyl)amino]hexyl]amino] benzenepropanoic acid (0.147 mol) are obtained.

Yield: 59% m.p.: 120° C. (dec.). K.F.: 0.26% (w/w).

| Elemental analysis | | | | |
|---|---|---|---|---|
| | C | H | I | N |
| % calc.: | 36.18 | 4.83 | 42.47 | 9.38 |
| % found: | 36.39 | 5.05 | 41.17 | 9.40 H₂O 0.26 |

TLC: silica gel plate 60F 254 Merck. Eluent: CHCl₃: AcOH: H₂O=3:5:1. Detector: UV light (254 nm) Rf=0.40. ¹H-NMR, ¹³C-NMR, IR and MS spectra are consistent with the assigned structure.

B) α-ethyl-2,4,6-triiodo-3-[[1-oxo-6-[[4,7,10-tris (carboxymethyl)-1,4,7,10-tetraazacyclododec-1-yl-acetyl] amino]hexyl]amino]benzenepropanoic acid According to the procedure described in Example 2, 111 g of compound (A) α-ethyl-2,4,6-triiodo-3-[[1-oxo-6-[(1,4,7,10-tetraazacyclododec-1-yl-acetyl)amino]hexyl]amino]benzenepropanoic acid (0.12 mol) are reacted with 67.2 g of bromoacetic acid (0.48 mol) in 600 ml of 80% EtOH. 63 g of α-ethyl-2,4,6-triiodo-3-[[1-oxo-6-[[4,7,10-tris(carboxymethyl)-1,4,7,10-tetraazacyclododec-1-ylacetyl]amino]hexyl]amino]benzenepropanoic acid (0.058 mol) are obtained.

Yield: 48% m.p.: 198° C. (dec.). Complexometric assay (0.1N ZnSO$_4$): 96.8%. K.F.: 1.30% (w/w).

| Elemental analysis | | | | |
|---|---|---|---|---|
| | C | H | I | N |
| % calc.: | 37.03 | 4.61 | 35.56 | 7.85 |
| % found: | 36.26 | 4.86 | 34.84 | 7.71 | H$_2$O 1.30 |

$^1$H-NMR, $^{13}$C-NMR, IR and MS spectra are consistent with the assigned structure.

C) Gadolinium complex of α-ethyl-2,4,6-triiodo-3-[[1-oxo-6-[[4,7,10-tris(carboxymethyl)-1,4,7,10-tetraazacyclododec-1-ylacetyl]amino]hexyl]amino]benzenepropanoic acid salified with 1-deoxy-1-(methylamino)-D-glucitol (1:1)

According to the procedure described in Example 1, 36.4 g of compound (B) α-ethyl-2,4,6-triiodo-3-[[1-oxo-6-[[4,7,10-tris(carboxymethyl)-1,4,7,10-tetraazacyclododec-1-ylacetyl]amino]hexyl]amino]benzenepropanoic acid (0.033 mol) in 400 ml of H$_2$O are reacted with 12.3 g of GdCl$_3$.6H$_2$O (0.033 mol) and 68.8 ml of an aqueous solution of 1N N-methylglucamine (0.0688 mol). 45 g of gadolinium complex of α-ethyl-2,4,6-triiodo-3-[[1-oxo-6-[[4,7,10-tris(carboxymethyl)-1,4,7,10-tetraazacyclododec-1-ylacetyl]amino]hexyl]amino]benzenepropanoic acid salified with 1-deoxy-1-(methylamino)-D-glucitol (1:1) (0.0309 mol) are obtained.

Yield: 94% m.p.: 225° C (dec.). K.F.: 2.39%.

| Elemental analysis | | | | | |
|---|---|---|---|---|---|
| | C | H | Gd | I | N |
| % calc.: | 33.84 | 4.47 | 11.07 | 26.81 | 6.90 |
| % found: | 33.13 | 4.77 | 10.69 | 26.06 | 6.71 | H$_2$O 2.39 |

EXAMPLE 7

Gadolinium complex of α-ethyl-2,4,6-triiodo-3-[[1-oxo-6-[[1-oxo-3-(phenylmethoxy)-2-4,7,10-tris(carboxymethyl)-(1,4,7,10-tetraazacyclododec-1-yl)propyl]amino]hexyl]amino]benzenepropanoic acid salified with 1-deoxy-1-(methylamino)-D-glucitol (1:1)

A) 6-[[2-chloro-3-phenylmethoxy)-1-oxopropyl]amino]hexanoic acid 233.1 g of 2-chloro-3-(phenylmethoxy)propanoyl chloride (CAS RN 124628-32-6) (1 mol) in 500 ml of THF are slowly added, during 3 h and keeping the temperature at 5°–10° C., to a solution of 157.4 g of 6-aminohexanoic acid (product commercially available) (1.2 mol) in 250 ml of H$_2$O. The solution pH is kept to 10 by adding 10N NaOH (tot. 200 ml, 2 mol). After 30 min. the solution is evaporated. The resulting precipitate is dissolved in H$_2$O and treated with 37% HCl, yielding a new precipitate. Recrystallization in Et$_2$O gives 275.5 g of 6-[[2-chloro-3-phenylmethoxy)-1-oxopropyl]amino]hexanoic acid (0.84 mol).

Yield: 84%. Acidimetric assay (0.1N NaOH): 94.2%. K.F.: 0.45% (w/w).

| Elemental analysis | | | | |
|---|---|---|---|---|
| | C | H | Cl | N |
| % calc.: | 58.62 | 6.76 | 10.82 | 4.27 |
| % found: | 58.84 | 7.05 | 10.60 | 4.53 | H$_2$O 0.45 |

$^1$H-NMR $^{13}$C-NMR IR and MS spectra are consistent with the assigned structure.

B) 3-[6-[[2-chloro-3-amino-3-(phenylmethoxy)-1-oxopropyl]amino]-1-oxohexyl]-α-ethyl-2,4,6-triiodobenzenepropanoic acid sodium salt According to the procedure described in Example 2, 88.7 g of the compound (A) 6-[[2-chloro-3-phenylmethoxy)-1-oxopropyl]amino]hexanoic acid (0.27 mol) in 300 ml of MeCN, 20.5 g of pyridine (0.26 mol) and the mixture of 10.0 g of DMF (0.26 mol) and 47.0 g of oxalyl chloride (0.37 mol), are reacted with 114.2 g of 3-amino-α-ethyl-2,4,6-triiodobenzenepropanoic acid (CAS RN 96-83-3) (0.27 mol) in 300 ml of MeCN. 38.6 g of 3-[6-[[2-chloro-3-amino-3-(phenylmethoxy)-1-oxopropyl]amino]-1-oxohexyl]-α-ethyl-2,4,6-triiodobenzenepropanoic acid sodium salt (0.0424 mol) are obtained.

Yield: 21% m.p.: 125° C. K.F.: 0.67% (w/w).

| Elemental analysis | | | | | |
|---|---|---|---|---|---|
| | C | H | Cl | I | N |
| % calc.: | 36.82 | 3.46 | 3.93 | 42.17 | 3.10 |
| % found: | 35.79 | 3.87 | 3.79 | 41.58 | 3.07 | H$_2$O 0.67 |

$^1$H-NMR, $^{13}$C-NMR, IR and MS spectra are consistent with the assigned structure.

C) α-ethyl-2,4,6-triiodo-3-[[1-oxo-6-[[1-oxo-3-(phenylmethoxy)-2-(1,4,7,10-tetraazacyclododec-1-yl)propyl]amino]hexyl]amino]benzenepropanoic acid According to the procedure described in Example 3, 48.2 g of 1,4,7,10-tetraazacyclododecane (0.28 mol) in 350 ml of DMSO are added to a suspension of 61.6 g of compound (B) 3-[6-[[2-chloro-3-amino-3-(phenylmethoxy)-1-oxopropyl]amino]-1-oxohexyl]-α-ethyl-2,4,6-triiodobenzenepropanoic acid sodium salt (0.07 mol). 37.5 g of α-ethyl-2,4,6-triiodo-3-[[1-oxo-6-[[1-oxo-3-(phenylmethoxy)-2-(1,4,7,10-tetraazacyclododec-1-yl)propyl]amino]hexyl]amino]benzenepropanoic acid (0.037 mol) are obtained.

Yield: 53% m.p.: 144° C. (153 ° C. dec.)
Acidimetric assay (HCl 0.1N) 94.8%

| Elemental analysis | | | | | |
|---|---|---|---|---|---|
| | C | H | I | N | Cl |
| % calc.: | 41.35 | 5.06 | 37.45 | 8.27 | |
| % found: | 41.98 | 5.33 | 37.01 | 8.13 | <0.10 |

$^1$H-NMR, $^{13}$C-NMR, IR and MS spectra are consistent with the assigned structure.

D) α-ethyl-2,4,6-triiodo-3-[[1-oxo-6-[[1-oxo-3-(phenylmethoxy)-2-4,7,10-tris(carboxymethyl)-(1,4,7,10-tetraazacyclododec-1-yl)propyl]amino]hexyl]amino]benzene propanoic acid According to the procedure described in Example 3, 16.7 g of bromoacetic acid (0.12 mol) in 30 ml of H$_2$O are reacted with 30.5 g of compound (C) (0.03 mol) in 50 ml of EtOH and 100 ml of H$_2$O. 25.1 g of α-ethyl-2,4,6-triiodo-3-[[1-oxo-6-[[1-oxo-3-(phenylmethoxy)-2-4,7,10-tris(carboxymethyl)-(1,4,7,10-tetraazacyclododec-1-yl)propyl]amino]hexyl]amino]benzenepropanoic acid (0.021 mol) are obtained.

Yield: 70%. Acidimetric assay (0.1N NaOH) 99.7%.

| | Elemental analysis | | | | | |
|---|---|---|---|---|---|---|
| | C | H | I | N | Na | Cl |
| % calc.: | 41.36 | 4.83 | 31.98 | 7.06 | | |
| % found: | 41.39 | 5.15 | 31.12 | 7.30 | 0.16 | <0.10 |

$^1$H-NMR, $^{13}$C-NMR, IR and MS spectra are consistent with the assigned structure.

E) Gadolinium complex of α-ethyl-2,4,6-triiodo- 3-[[1-oxo-6-[[1-oxo-3-(phenylmethoxy)-2,4,7,10-tris(carboxymethyl)-(1,4,7,10-tetraazacyclododec-1-yl)propyl]amino]hexyl]amino]benzenepropanoic acid salified with 1-deoxy-1-(methylamino)-D-glucitol (1:1)

According to the procedure described in Example 1, 23.87 g of compound (D) 3-[[6-[[[4,7,10-tris(carboxymethyl)-1,4,7,10-tetraazacyclododec-1-yl]-2-[(phenyl methoxy)methyl] acetyl]amino]-1-oxohexyl]amino]-2,4,6-triiodobenzoic acid (0.02 mol) in 300 ml of H$_2$O are reacted with 7.4 g of GdCl$_3$.6H$_2$O (0.02 mol) and 73.2 ml of a aqueous solution of 1N N-methylglucamine (0.073 mol). 22.8 g of gadolinium complex of α-ethyl-2,4,6-triiodo-3-[[1-oxo-6-[[1-oxo-3-(phenylmethoxy)-2-4,7,10-tris(carboxymethyl)-(1,4,7,10-tetraazacyclododec-1-yl)propyl]amino]hexyl]amino] benzenepropanoic acid salified with 1-deoxy-1-(methylamino)-D-glucitol (1:1) (mol) are obtained.

Yield: 74% m.p.: 185°–190° C.

| | Elemental analysis | | | | |
|---|---|---|---|---|---|
| | C | H | Gd | I | N |
| % calc.: | 37.43 | 4.65 | 10.21 | 24.72 | 6.37 |
| % found: | 37.96 | 4.90 | 10.14 | 24.44 | 6.30 | H$_2$O 1.46 |

The following compound was prepared according to the same procedure:
gadolinium complex of 18-[[3-(2-carboxybutyl) -2,4,6-triiodophenyl]amino]-3,6,9-tris(carboxymethyl)-11,18-dioxo-10-(phenylmethoxy)methyl-3,6,9,12-tetraazaoctadecanoic acid salified with 1-deoxy-1-(methylamino)-D-glucitol (N-methylglucamine) (1:2) (Compound 11).

EXAMPLE 8

Gadolinium complex of 3,3'-[(carboxymethyl)imino-bis[ [(2,1-ethanediyl)carboxymethyl)imino](1-oxo-2,1-ethanediyl)imino(1-oxo-6,1-hexanediyl)imino]]bis-2,4,6-triiodobenzoic acid] salified with 1-deoxy-1-(methyl-amino) -D-glucitol (N-methylglucamine) (1:2)

A) 3- [(2-aminoacetyl)amino]-2,4,6-triiodobenzoic acid 6.34 g of 3-[(2-chloroacetyl)amino]-2,4,6-triiodobenzoic acid (prepared as described in Example 3) (10.72 mmol) are dissolved in 250 ml of 25% NH$_4$OH and the solution is kept in autoclave for 35 hours at r.t. The mixture is evaporated to dryness and the residue is then dissolved in H$_2$O, adjusting the pH to 7 and yielding a precipitate, which is filtered. 5.74 g of 3-[(2-aminoacetyl)amino]-2,4,6-triiodobenzoic acid (10.04 mmol) are obtained.

Yield: 98.4%. $^1$H-NMR, $^{13}$C-NMR, IR and MS spectra are consistent with the assigned structure.

B) 3,3'-[(carboxymethyl)iminobis[[(2,1-ethanediyl)-carboxymethyl)imino](1-oxo-2,1-ethanediyl)imino (1-oxo-6,1-hexanediyl)imino]]bis-2,4,6-triiodobenzoic acid]

20 g of the compound (A) 3-[(2-aminoacetyl)amino]-2,4,6-triiodobenzoic acid (35 mmol) are suspended in 100 ml H$_2$O and 37 ml 1M NaOH are added to obtain a solution. Then the pH is adjusted to 9 with HCl and 6.2 g of diethylenetriamine-N,N',N'',N''-pentaacetic acid anhydride (product commercially available) (17.5 mmol) are added at once. Immediately the pH changes to 3 and a precipitate is obtained, which is filtered. The residue is purified by passing through Amberlite® XAD 16 with MeOH:H$_2$O=70:30. After evaporation to dryness, 17 g of 3,3'-[(carboxymethyl) iminobis[[(2,1-ethanediyl)-carboxymethyl)imino](1-oxo-2,1-ethanediyl)imino (1-oxo-6,1-hexanediyl)imino]]bis-2,4,6-triiodobenzoic acid] (11.32 mmol) are obtained.

Yield: 65%.

| | Elemental analysis | | | | |
|---|---|---|---|---|---|
| | C | H | I | N | |
| % calc.: | 25.60 | 2.20 | 50.72 | 6.53 | |
| % found: | 25.16 | 2.40 | 49.25 | 6.51 | H$_2$O 3.54 |

$^1$H-NMR, $^{13}$C-NMR, IR and MS spectra are consistent with the assigned structure.

C) Gadolinium complex of 3,3'-[(carboxymethyl)imino-bis [[[(2,1-ethanediyl)carboxymethyl)imino](1-oxo-2,1-ethanediyl)imino (1-oxo-6,1-hexanediyl)imino]]-bis-2,4,6-triiodobenzoic acid]salified with 1-deoxy-1-(methylamino)-D-glucitol (N-methylglucamine) (1:2)

1 g of compound (B) 3,3'-[(carboxymethyl)iminobis-[[(2,1-ethanediyl)carboxymethyl)imino](1-oxo-2,1-ethanediyl) imino (1-oxo-6,1-hexanediyl)imino]]bis-2,4,6-triiodobenzoic acid] (0.65 mmol) is suspended in 50 ml H$_2$O and 0.254 g of 1N N-methylglucamine (1.30 mmol) are added. Then 0.118 g of GdO$_3$ (0.32 mmol) are added and the solution is heated at 60 ° C. for 24 h. After evaporation to dryness, 1.33 g of gadolinium complex of 3,3'-[ (carboxymethyl)iminobis[[(2,1-ethanediyl)carboxymethyl) imino](1-oxo-2,1-ethanediyl)imino (1-oxo-6,1-hexanediyl) imino]]bis-2,4,6-triiodobenzoic acid] salified with 1-deoxy-1-(methylamino)-D-glucitol (N-methyl-glucamine) (1:2) (0.065 mmol) are obtained.

Yield: 100%.

| | Elemental analysis | | | | |
|---|---|---|---|---|---|
| | C | H | Gd | I | N |
| % calc.: | 26.97 | 3.30 | 7.67 | 37.16 | 6.15 |
| % found: | 26.86 | 3.16 | 7.72 | 37.30 | 5.98 |

TLC: silica gel plate 60F 254 Merck. Eluent: CHCl$_3$: MeOH: 25%NH$_4$OH=5:3.5:1.5. Detector: UV light (254 nm) Rf=0.30.

EXAMPLE 9

The relaxivities r$_1$ and r$_2$ (mM$^{-1}$.$^{-1}$) of gadolinium complexes of some of the preferred compounds of this invention are determined in a 0.15M NaCl solution in water, in a magnetic field of frequency of 20 MHz, at a temperature of 39° C., (MINISPEC PC-120 device), using the following sequence: Saturation Recovery; Inversion Recovery;

CPMG; and compared to those of Gd-DTPA/Dimeg (Magnevist® and Gd-DOTA/meg (Dotarem® [percentage ratios are calculated with respect to Gd-DOTA/meg]. Experimental results are reported in Table 1.

TABLE 1

| Compounds | $A = \dfrac{r_1 \text{(Gd-compound)}}{r_1 \text{(Gd-DOTA)}}$ | | $B = \dfrac{r_2 \text{(Gd-compound)}}{r_2 \text{(Gd-DOTA)}}$ | |
|---|---|---|---|---|
| | $r_1$ (mM$^{-1}$ · s$^{-1}$) | A.100 | $r_2$ (mM$^{-1}$ · s$^{-1}$) | B.100 |
| Compound 1D | 5.91 | 166.0 | 7.96 | 167.6 |
| Compound 2D | 5.48 | 153.9 | 6.17 | 129.9 |
| Compound 3D | 5.01 | 140.7 | 7.03 | 148.0 |
| Compound 4E | 5.58 | 156.7 | 7.30 | 153.7 |
| Compound 5D | 4.80 | 134.8 | 6.25 | 131.6 |
| Compound 6C | 5.07 | 142.4 | 6.60 | 138.9 |
| Magnevist$^{(R)}$ | 3.77 | 105.9 | 4.73 | 99.6 |
| Dotarem$^{(R)}$ | 3.56 | 100.0 | 4.75 | 100.0 |

EXAMPLE 10

The radioscopic examination (1 rat/dose) is performed at 50 kV and 0.8 mA.

Compound 1D (Example 1)

dose 0.25 mmol/kg: visualization of the bladder (after 10–20 min.), of the duodenum (after 20 min) and of the small intestine (after 60 min);

dose 0.5 mmol/kg: visualization of the bladder and duodenum (after 20 min) of the left kidney and left urethra (after 240 min).

Compound 2D (Example 2)

dose 0.25 mmol/kg: visualization of the bladder and duodenum ( after 5 min.) and of the large intestine (after 5 h);

dose 0.5 mmol/kg: visualization of the bladder and duodenum (after 5 min) and of the small intestine (after 3 h) and of the large intestine (after 4 h).

Compound 5D (Example 5)

dose 0.25 mmol/kg: visualization of the only bladder after 5 min;

dose 0.5 mmol/kg: visualization of the renal pelvis and urethra and bladder (after 120 min),

Compound 6C (Example 6)

dose 0.25 mmol/kg: visualization of the renal pelvis and urethra ( after 45 min.) and of the bladder and small intestine (after 60 min);

dose 0.5 mmol/kg: visualization of the duodenum (after 60 min) and small intestine (after 240 min).

What is claimed is:

1. Compounds of general formula (Ia) and (Ib)

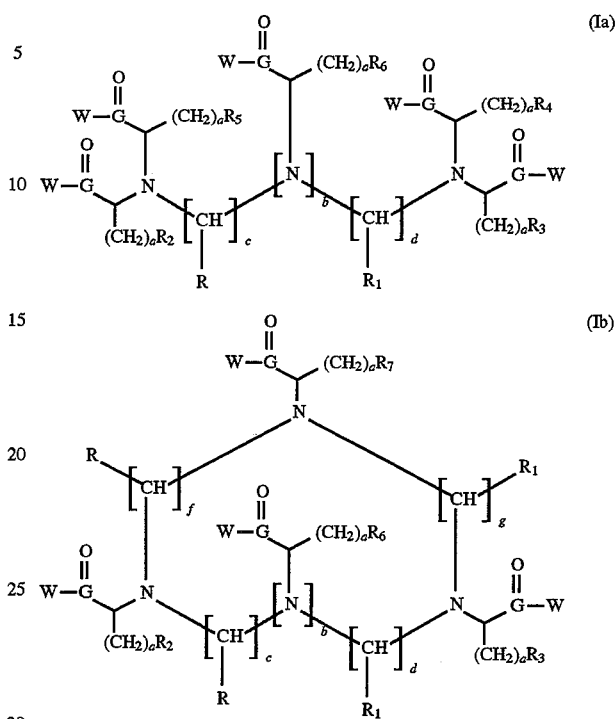

wherein:

a, b which are the same or different are 0 or 1, c, d which are the same or different, can be an integer from 1 to 4, f, g which are the same or different are an integer from 2 to 4, R, $R_1$ which are the same or different, are H, or a $C_1$–$C_8$ straight, branched or alicyclic alkyl group, or a $C_1$–$C_6$ straight or branched hydroxyalkyl group, containing 1–5 OH groups, or an alkoxyalkyl or hydroxyalkoxy alkyl group, or they are one aryl, alkylaryl, aryloxy, benzyloxy or heteroaryl residue, where the aromatic nucleus is substituted or not by one or more halogen, alkyl, hydroxyalkyl, hydroxyl, alkoxyl, trifluoromethyl, carboxyl, amino, carbamoyl, anilido, cyano, thiocyano, nitro, mercapto, thioalkyl, sulforyl, sulfonyl, phosphoryl, phosphonyl group, or R and $R_1$, taken together, are a trimethylene or tetraethylene residue, $R_2$–$R_7$ which are the same or different, are H, or a $C_1$–$C_8$ straight, branched or alicyclic alkyl group, or a $C_1$–$C_8$ alkoxyalkyl group, or a group of formula —$CH_2$—O— Y, where the residue Y is H, a $C_1$–$C_8$ straight, branched or alicyclic alkyl group, or an aryl, alkylaryl or heteroaryl nucleus, in which the aromatic nucleus is substituted or not by one or more ha logen, alkyl, hydroxyalkyl, hydroxyl, alkoxyl, trifluoromethyl, carboxyl, amino, carbamoyl, anilido, cyano, thiocyano, nitro, mercapto, thioalkyl, sulforyl, sulfonyl, phosphoryl, phosphonyl group, or the substituents from $R_2$ to $R_7$ can be the residue Z of formula: —$(CH_2)_h$—$(CO)_i$—$(NR_8)_l$—$(CH_2)_m$—$(CO)_n$—$(L)_p$—B wherein:

h,i,l,n,p are integers from 0 to 1, m is an integer from 0 to 20,

B is an X-ray opaque, ionic or non-ionic, aromatic or heteroaromatic residue, containing at least a functionalized iodinated aromatic nucleus, being said B group bound to the remaining part of Z through one of the non-iodinated positions of the aromatic nucleus, L is —$NR_8$— or —O— and $R_8$ is H, or residue of formula —$(CH_2)_m$—$(CO)_n$—$(NH)_p$—B, wherein m, n, p and B are as above defined, G is a carbon, sulfur, phosphorus atom, or —SO—, —$SO_2$—, —PO—, —$PO_2$—, W is H, or one of the groups: Z, —O—$R_9$ or —$N(R_{10})$—$(CH_2)_q$—$R_{11}$, wherein:

Z is as above defined, $R_9$ is H or a $C_1$–$C_8$ straight, branched or alicyclic alkyl group, or a $C_1$–$C_6$ straight, branched hydroxyalkyl group, containing 1–5 OH groups, or an alkoxyalkyl or hydroxyalkoxy alkyl group, or $R_9$ is a polyoxaalkyl residue containing from 1 to 15 oxygen atoms and from 3 to 45 carbon atoms, q is an integer from 0 to 6, $R_{10}$ equal or different from $R_{11}$, is H or a $C_1$–$C_8$ straight, branched or alicyclic alkyl group, or a $C_1$–$C_6$ straight, branched hydroxyalkyl group, containing 1–5 OH groups, or an alkoxyalkyl or alkoxyhydroxyalkyl group, or a residue Z as above defined, $R_{11}$ is defined as $R_{10}$ and in addition, when q is different from 0, it can also be one of the two groups —CO—$NR_{12}R_{13}$ or —$NR_{12}R_{13}$ wherein $R_{12}$ and $R_{13}$ are defined as $R_{10}$ and $R_{11}$, and when q is equal to 0, then $R_{10}$ and $R_{11}$ can be bound together to represent a $C_2$–$C_6$ alkylene group which can be interrupted by —O—, —S—, —N— atoms, with the proviso that, at least one of the substituents from $R_2$ to $R_7$ must be a residue Z, or at least one of the groups W must be or include a residue Z, and the chelate complexes of said compounds of formula (Ia) and (Ib) with ions of metal elements with atomic number from 20 to 31, 39, from 42 to 44, 49 and from 57 to 83, and the salts thereof with physiologically tolerable organic bases, selected from primary, secondary or tertiary amines or basic aminoacids, or with inorganic bases whose cations are sodium, potassium, magnesium, calcium or mixtures of the same.

2. Compounds according to claim 1, of general formula (IIa), (IIb), (IIc)

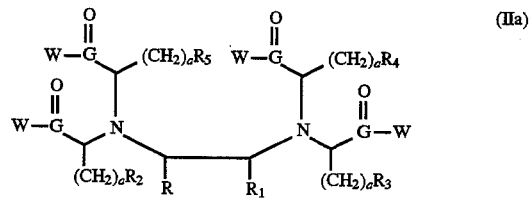

(IIa)

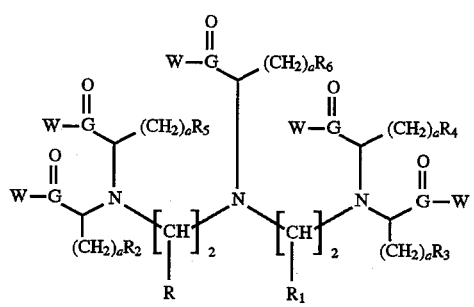

(IIb)

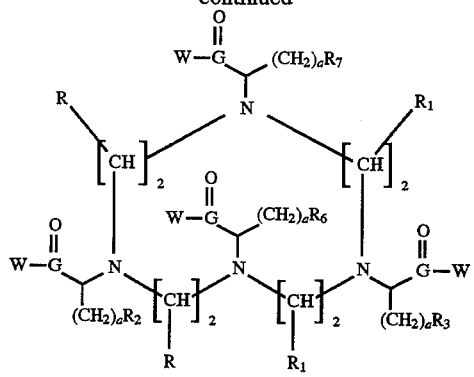

(IIc)

wherein a, R, $R_1$, $R_2$, $R_3$, $R_4$, $R_5$, $R_7$, G, W are as above defined, with the proviso that at least one of the substituents from $R_2$ to $R_7$ must be a residue Z, as above defined, or at least one of the W groups is or includes said residue Z, and the chelate complexes of said compounds of formula (IIa), (IIb), (IIc) with ions of metal elements with atomic number included from 20 to 31, 39, from 42 to 44, 49 and from 57 to 83 and their salts with physiologically tolerable organic bases, selected from primary, secondary or tertiary amines or basic aminoacids, or with inorganic bases whose cations are sodium, potassium, magnesium, calcium or mixtures of the same.

3. Compounds according to claim 1, in which the iodinated radiopaque component B includes at least one triiodinated aromatic or heteroaromatic residue bound to the remaining part of the molecule, through one of the non-iodinated positions of the aromatic or heteroaromatic nucleus.

4. Compounds according to claim 3, in which the iodinated radiopaque component B comprises the residue of any iodinated X-ray contrast agent, both ionic and nonionic, monomeric and dimeric.

5. Compounds according to claim 3, in which the X-ray opaque component is selected from acetrizoic acid, diprotrizoic acid, iobenzamic acid, iobutoic acid, iocarmic acid, iocetamic acid, iopanoic acid, iopronic acid, iothalamic acid, diatrizoic acid, iodoxamic acid, ioglycic acid, ioglycamic acid, iolidonic acid, iolixanic acid, iomorinic acid, iopromic acid, iosefamic acid, ioseric acid, iotetric acid, iotrizoic acid, iotroxic acid, ioxaglic acid, metrizoic acid, iodamide, iodipamide, iopamidol, iomeprol, iohexol, ioversol, metrizamide, iotrolan, iodecimol, iodixanol, ioglucol, ioglucomide, ioglunide, iogulamide, iopentol, iopydol, iopyrol, iopromide, iosarcol, iosimide, iotasul, iotriside, ioxilan, iofratol.

6. Compounds according to claim 1, in which the chelating component include at least the structural residue of an acyclic or cyclic aminopolycarboxylic acid, or the residue of a aminopolyphosphonic, aminopolyphosphinic, aminopolysulfonic, aminopolysulfinic acid and/or their derivatives.

7. Compounds according to claim 6, in which the chelating residue is selected from EDTA, DTPA, DTPA-bismethylamide, DTPA hydroxyalkylamides, DOTA, DOTMA, DO3A, HP-DO3A, BOPTA, DPDP, EOB-DTPA, BT-DO3A, MCTA.

8. Compounds according to claim 1, in which the paramagnetic metal ion is selected from $Fe^{(2+)}$, $Fe^{(3+)}$, $Mn^{(2+)}$, $Gd^{(3+)}$, $Eu^{(3+)}$, $Dy^{(3+)}$, $La^{(3+)}$, $Yb^{(3+)}$.

9. Compounds according to claim 8, in which the paramagnetic metal ion is $Gd^{(3+)}$.

10. Compounds according to claim 1, in which the salifying physiologically tolerable organic base is selected from ethanolamine, diethanolamine, morpholine, glucamine, N, N-methylglucamine, N-methylglucamine, lysine, arginine, ornitine.

11. Contrast agent for the preparation of diagnostic formulations to obtain images of organs and/or tissues of human and animal body through the use of nuclear magnetic resonance or X-rays or the combination of both techniques, including at least one of the compounds of formula (Ia), (Ib), (IIa), (IIb), (IIc), or a salt thereof, as defined in claim 1.

12. Pharmaceutical contrast formulations to obtain images of organs and/or tissues of human and animal body through the use of nuclear magnetic resonance or X-rays or the combination of both techniques, including at least one of the compounds of formula (Ia), (Ib), (IIa), (IIb), (IIc), or a salt thereof, as defined in claim 1.

13. The compound according to claim 2 which is the gadolinium complex of 18-[[3-(2-carboxybutyl)-2,4,6-triiodophenyl]amino]-3,6,9-tris(carboxymethyl)-11,18-dioxo-3,6,9,12-tetraazaoctadecanoic acid salified with 1-deoxy-1-(methylamino)-D-glucitol (N-methylglucamine) (1:2).

14. The method of obtaining images of organs, tissues and both organs and tissues of human animal body through the use of nuclear magnetic resonance or x-rays or the combination of both nuclear magnetic resonance and x-rays which consists of providing a formulation comprising a compound of formula (Ia) or (Ib)

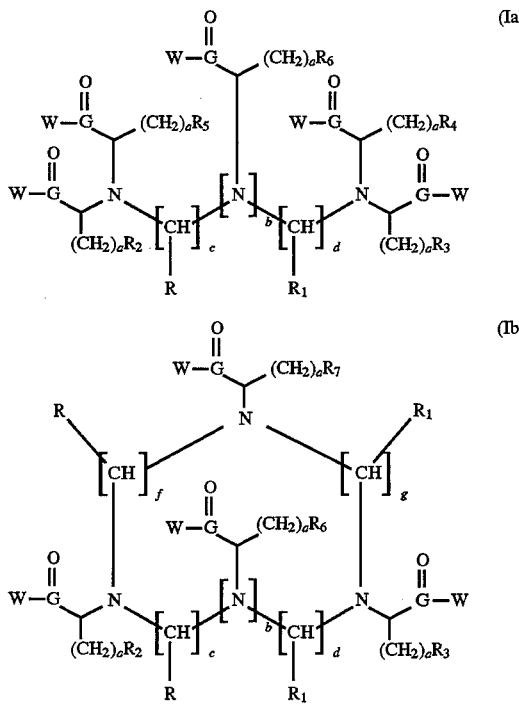

wherein:

a, b are the same or different and are 0 or 1, c, d are the same or different and are an integer from 1 to 4, f, g are the same or different and are an integer from 2 to 4, R, $R_1$ are the same or different and are H, or a $C_1$–$C_8$ straight, branched or alicyclic alkyl group or a $C_1$–$C_6$ straight or branched hydroxyalkyl group, containing 1–5 OH groups, or an alcoxyalkyl or hydroxyalcoxy alkyl group, or are aryl, alkylaryl, aryloxy, benzyloxy or heteroaryl residue, wherein the aromatic nucleus is unsubstituted or substituted by at least one halogen, alkyl, hydroxyalkyl, hydroxyl, alcoxyl, trifluoromethyl, carboxyl, amino, carbamoyl, anilido, cyano, thiocyano, nitro, mercapto, thioalkyl, sulfuryl, sulfonyl, phosphoryl, phosphonyl group, or R and $R_1$, taken together, are a trimethylene or tetramethylene residue, $R_2$–$R_7$ are the same or different, and are H, or a $C_1$–$C_8$ straight, branched or alicyclic alkyl group, or a $C_1$–$C_8$ alcoxyalkyl group, or a group of formula —$CH_2$—O—Y, wherein the residue Y is H, a $C_1$–$C_8$ straight, branched or alicyclic alkyl group, or an aryl, alkylaryl or heteroaryl nucleus, in which the aromatic nucleus is unsubstituted or substituted by at least one halogen, alkyl, hydroxyalkyl, hydroxyl, alcoxyl, trifluoromethyl, carboxyl, amino, carbamoyl, anilido, cyano, thiocyano, nitro, mercapto, thioalkyl, sulfuryl, sulfonyl, phosphoryl, phosphonyl group, or the substituents from $R_2$ to $R_7$ are the residue Z of formula:

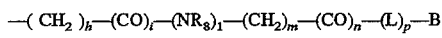

wherein:

h,i,l,n,p are integers from 0 to 1, m is an integer from 0 to 20,

B is an X-ray opaque, ionic or non-ionic, aromatic or heteroaromatic residue, containing at least a functionalized iodinated aromatic nucleus, said B group being bound to the remaining part of Z through one of the non-iodinated positions of the aromatic nucleus, L is —$NR_8$— or —O— and $R_8$ is H, or a residue of formula —$(CH_2)_m$—$(CO)_n$—$(NH)_p$—B, wherein m, n, p and B are as above defined, G is a carbon, sulfur, phosphorus atom, or —SO—, —$SO_2$—, —PO—, —$PO_2$—, W is H, or one of the groups: Z, —O—$R_9$ or —N($R_{10}$)—$(CH_2)_q$—$R_{11}$, wherein:

Z is as above defined, $R_9$ is H or a $C_1$–$C_8$ straight, branched or alicyclic alkyl group, or a $C_1$–$C_6$ straight, branched hydroxyalkyl group, containing 1–5 OH groups, or an alcoxyalkyl or hydroxyalcoxy alkyl group, or $R_9$ is a polyoxaalkyl residue containing from 1 to 15 oxygen atoms and from 3 to 45 carbon atoms, q is an integer from 0 to 6, $R_{10}$ is equal or different from $R_{11}$, and is H or a $C_1$–$C_8$ straight, branched or alicyclic alkyl group, or a $C_1$–$C_6$ straight, branched hydroxyalkyl group, containing 1–5 OH groups, or an alcoxyalkyl or alcoxyhydroxyalkyl group, or a residue Z as above defined, $R_{11}$ is defined as $R_{10}$ and in addition, when q is different from 0, it is one of the two groups —CO—$NR_{12}R_{13}$ or —$NR_{12}R_{13}$ wherein $R_{12}$ and $R_{13}$ are defined as $R_{10}$ and $R_{11}$, and when q is equal to 0, then $R_{10}$ and $R_{11}$ are bound together to represent a $C_2$–$C_6$ alkylene group, said $C_2$–$C_6$ alkylene group being as such or being interrupted by an —O—, a —S—, or a —N— atom, with the proviso that at least one of the substituents from $R_2$ to $R_7$ must be a residue Z, or at least one of the groups W must be or include a residue Z, and the chelate complexes of said compounds of formula (Ia) and (Ib) with ions of metal elements with atomic number from 20 to 31, 39, from 42 to 44, 49 and from 57 to 83, and the salts thereof with physiologically tolerable organic bases, selected from primary, secondary or tertiary amines or basic aminoacids, or with inorganic bases whose cations are sodium, potassium, magnesium, calcium or mixtures thereof.
15. The method according to claim 14 wherein said compound has the formula (IIa), (IIb) or (IIc)
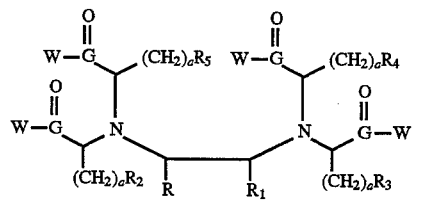
(IIa)
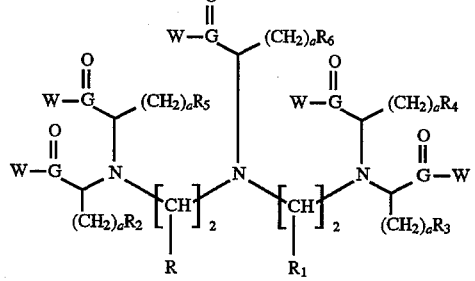
(IIb)
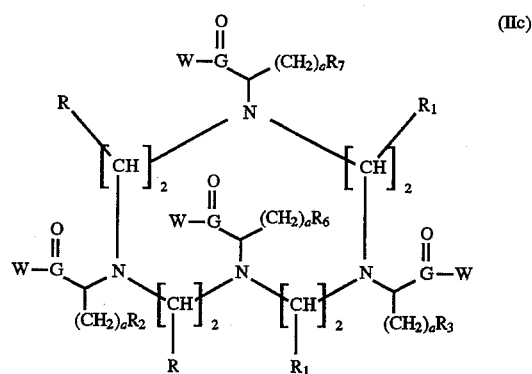
(IIc)
wherein a, R, $R_1$, $R_2$, $R_3$, $R_4$, $R_5$, $R_7$, G, W are as above defined.
* * * * *